United States Patent
Nakagawa et al.

(10) Patent No.: US 12,163,886 B2
(45) Date of Patent: *Dec. 10, 2024

(54) INFORMATION PROCESSING APPARATUS, INFORMATION PROCESSING METHOD, INFORMATION PROCESSING SYSTEM, AND COMPUTER PROGRAM

(71) Applicant: Sony Group Corporation, Tokyo (JP)

(72) Inventors: Kazuhiro Nakagawa, Saitama (JP); Ayumu Taguchi, Tokyo (JP); Hideya Chubachi, Kanagawa (JP)

(73) Assignee: Sony Group Corporation, Tokyo (JP)

(*) Notice: Subject to any disclaimer, the term of this patent is extended or adjusted under 35 U.S.C. 154(b) by 77 days.

This patent is subject to a terminal disclaimer.

(21) Appl. No.: 18/094,328

(22) Filed: Jan. 6, 2023

(65) Prior Publication Data
US 2023/0152231 A1 May 18, 2023

Related U.S. Application Data

(63) Continuation of application No. 17/260,964, filed as application No. PCT/JP2019/026916 on Jul. 5, 2019, now Pat. No. 11,579,090.

(30) Foreign Application Priority Data

Jul. 24, 2018 (JP) .................................. 2018-138663
Jan. 16, 2019 (JP) .................................. 2019-005402

(51) Int. Cl.
*G01N 21/64* (2006.01)
*G01N 33/58* (2006.01)

(52) U.S. Cl.
CPC ..... *G01N 21/6458* (2013.01); *G01N 21/6408* (2013.01); *G01N 21/6428* (2013.01); *G01N 33/582* (2013.01); *G01N 2201/12761* (2013.01)

(58) Field of Classification Search
None
See application file for complete search history.

(56) References Cited

U.S. PATENT DOCUMENTS

| | | |
|---|---|---|
| 5,324,633 A | 6/1994 | Fodor et al. |
| 6,259,524 B1 | 7/2001 | Hofstraat et al. |

(Continued)

FOREIGN PATENT DOCUMENTS

| | | |
|---|---|---|
| CN | 103454204 A | 12/2013 |
| EP | 3483592 A1 | 5/2019 |

(Continued)

OTHER PUBLICATIONS

U.S. Appl. No. 14/651,553, Nakagawa et al., filed Oct. 13, 2015

(Continued)

*Primary Examiner* — Marcus H Taningco
(74) *Attorney, Agent, or Firm* — Wolf, Greenfield & Sacks, P.C.

(57) ABSTRACT

Provided is an information processing apparatus (100) including: an image acquiring unit (112) that acquires captured image information of a sample (20) dyed with a fluorescent dye reagent (10), an information acquiring unit (111) that acquires information related to the fluorescent dye reagent (10), a correcting unit (131) that corrects the luminance of the captured image information using a fluorescence fading coefficient that represents the rapidness at which the fluorescence intensity of the fluorescent dye reagent (10) drops, the fluorescence fading coefficient being included in the fluorescent dye reagent (10), and a calculating unit (132) that calculates information corresponding to fluorescent molecules in the captured image information, using the corrected luminance.

20 Claims, 19 Drawing Sheets

(56) References Cited

U.S. PATENT DOCUMENTS

| | | | |
|---|---|---|---|
| 10,163,203 B2 | 12/2018 | Nakagawa et al. | |
| 10,209,236 B2 | 2/2019 | Nakagawa et al. | |
| 10,360,679 B2 | 7/2019 | Oshima et al. | |
| 10,482,598 B2 | 11/2019 | Nakagawa et al. | |
| 10,861,154 B2 | 12/2020 | Nakagawa et al. | |
| 10,922,815 B2 | 2/2021 | Oshima et al. | |
| 11,017,527 B2 | 5/2021 | Oshima et al. | |
| 11,579,090 B2* | 2/2023 | Nakagawa | G01N 21/6428 |
| 2003/0147133 A1 | 8/2003 | Engelhardt | |
| 2009/0117605 A1 | 5/2009 | Davis et al. | |
| 2012/0084013 A1 | 4/2012 | Davis et al. | |
| 2013/0230867 A1 | 9/2013 | Davis et al. | |
| 2015/0115176 A1 | 4/2015 | Watanabe et al. | |
| 2016/0041144 A1 | 2/2016 | Nakagawa et al. | |
| 2016/0284081 A1 | 9/2016 | Nakagawa et al. | |
| 2017/0186156 A1 | 6/2017 | Isoda | |
| 2017/0236277 A1 | 8/2017 | Oshima et al. | |
| 2019/0025213 A1 | 1/2019 | Abe | |
| 2019/0080452 A1 | 3/2019 | Nakagawa et al. | |
| 2019/0162667 A1 | 5/2019 | Ozaki et al. | |
| 2019/0259155 A1 | 8/2019 | Oshima et al. | |
| 2019/0362493 A1 | 11/2019 | Oshima et al. | |
| 2020/0098107 A1 | 3/2020 | Nakagawa et al. | |
| 2021/0325307 A1 | 10/2021 | Nakagawa et al. | |

FOREIGN PATENT DOCUMENTS

| | | |
|---|---|---|
| JP | H09-43147 A | 2/1997 |
| JP | 2001-201691 A | 7/2001 |
| JP | 2005-214728 A | 8/2005 |
| JP | 2008-520247 A | 6/2008 |
| JP | 2009-008603 A | 1/2009 |
| JP | 2011-247656 A | 12/2011 |
| JP | 2012-194013 A | 10/2012 |
| JP | 2013-025466 A | 2/2013 |
| JP | 2014-145632 A | 8/2014 |
| JP | 2014-161321 A | 9/2014 |
| JP | 2016-186446 A | 10/2016 |
| WO | WO 2006/055816 A2 | 5/2006 |
| WO | WO 2017/163427 A1 | 9/2017 |
| WO | WO 2018/008309 A1 | 1/2018 |

OTHER PUBLICATIONS

U.S. Appl. No. 15/033,089, Nakagawa et al., filed Apr. 28, 2016.
U.S. Appl. No. 15/502,252, Oshima et al., filed Feb. 7, 2017.
U.S. Appl. No. 16/188,151, Nakagawa et al., filed Nov. 12, 2018.
U.S. Appl. No. 16/315,323, Oshima et al., filed Jan. 4, 2019.
U.S. Appl. No. 16/433,998, Oshima et al., filed Jun. 6, 2019.
U.S. Appl. No. 16/656,428, Nakagawa et al., filed Oct. 17, 2019.
International Search Report and English translation thereof mailed Sep. 17, 2019 in connection with International Application No. PCT/JP2019/026916.
International Written Opinion and English translation thereof mailed Sep. 17, 2019 in connection with International Application No. PCT/JP2019/026916.
International Preliminary Report on Patentability and English translation thereof mailed Feb. 4, 2021 in connection with International Application No. PCT/JP2019/026916.
Extended European Search Report issued Aug. 13, 2021 in connection with European Application No. 19841590.3.
De Meyer et al., Contribution of data pre-processing to deconvolution of 3-D fluorescence microscopy images. SPIE. Biophotonics and New Therapy Frontiers Apr. 14, 2006(6191). 11 pages.
Nagelhus et al., Fading correction for fluorescence quantitation in confocal microscopy. Cytometry: The Journal of the International Society for Analytical Cytology. Mar. 1, 1996;23(3):187-95.
Nagy et al., Characterizing observation vols. and the role of excitation saturation in one-photon fluorescence fluctuation spectroscopy. Journal of biomedical optics. Aug. 2005;10(4):044015.
"It is desired to label a fluorescent dye" [online], A JPO Research Institute, Jan. 17, 2018, [search on Sep. 20, 2023], pp. 127-133.

* cited by examiner

FIG.9

| FLUORESCENT SUBSTANCE | QUANTUM YIELD ||
|---|---|---|
| | ACTUAL MEASUREMENTS | CATALOG SPECIFICATIONS |
| FITC | 0.097 | 0.590 |
| AF488 | 0.167 | 0.920 |
| BV711 | 0.001 | 0.150 |
| AF555 | 0.076 | 0.100 |
| AF647 | 0.103 | 0.330 |
| BV480 | 0.573 | 0.810 |
| PE | 0.483 | 0.840 |
| BV605 | 0.193 | 0.290 |

FIG.12
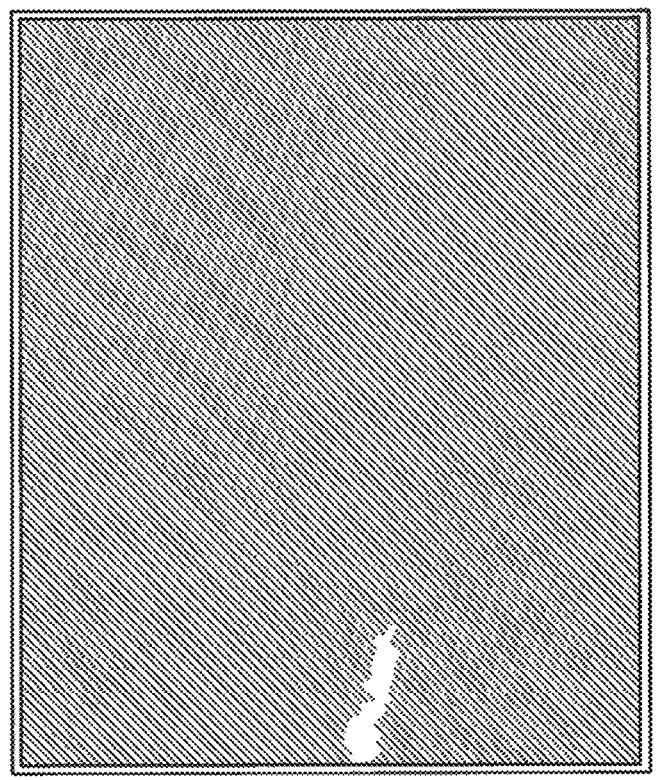
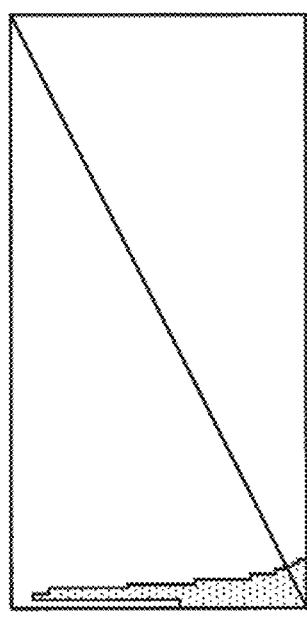

FIG.13
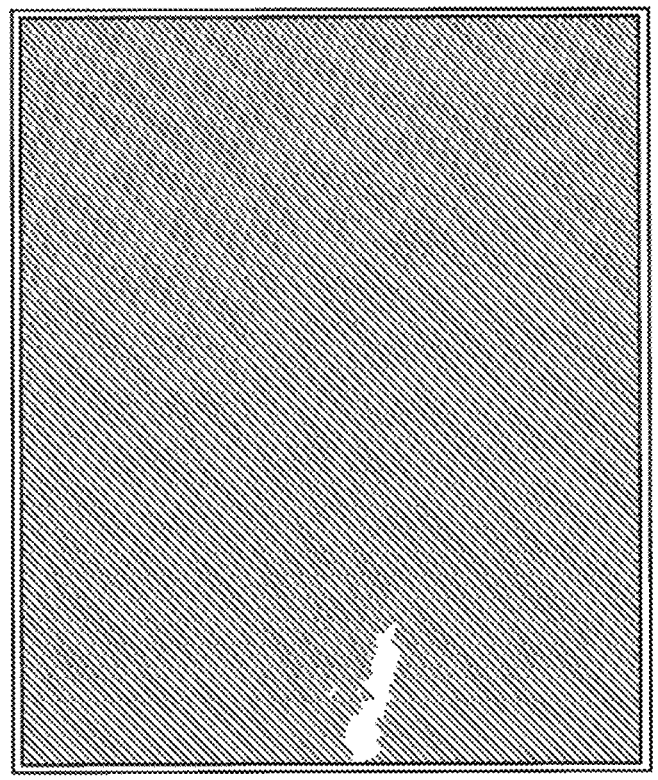
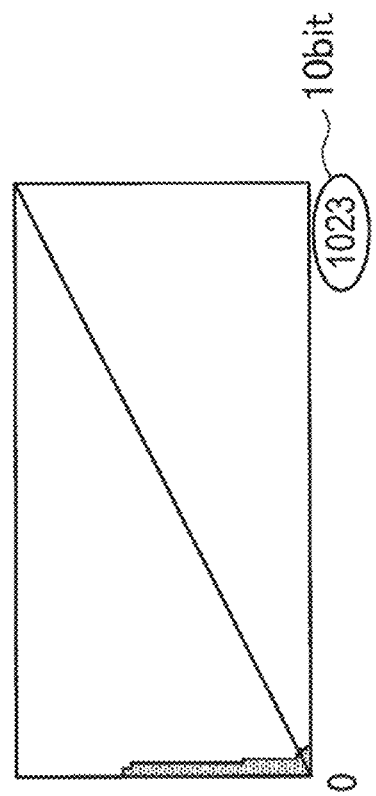

FIG.14
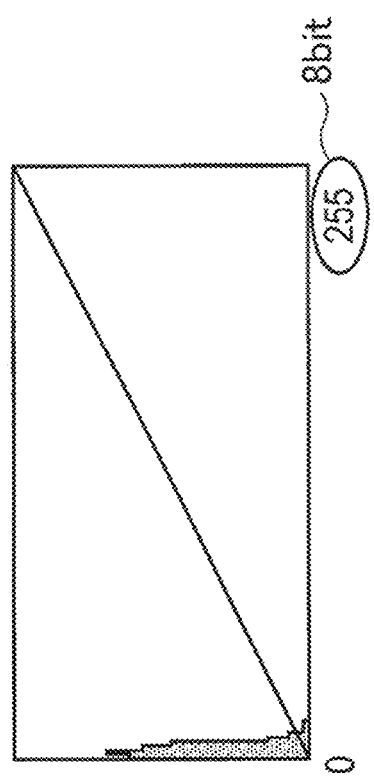
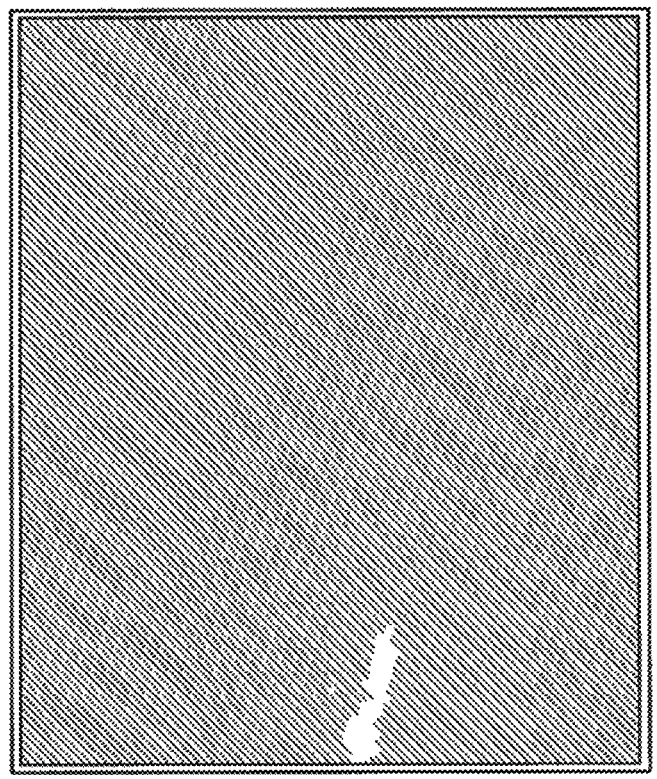

FIG.15

| FLUORESCENT SUBSTANCES | NUMBER OF PHOTONS PER ONE MOLECULE (THOSE DETECTABLE THROUGH OBJECTIVE LENS) [Photon/s/mW/cm$^2$] | IMAGE COMPRESSION RATIO WITH NUMBER OF FLUORESCENT MOLECULES | FLUORESCENT LABELING RATIO (F/P RATIO) | IMAGE COMPRESSION RATIO WITH NUMBER OF ANTIBODIES |
|---|---|---|---|---|
| FITC (Mouse IgG2b,k) | 3.99E-03 | 74.3% | 8.82 | 8.43% |
| AF488 (Mouse IgG1,k) | 7.47E-03 | 79.7% | 4.23 | 18.8% |
| BV711 (Mouse IgG1,k) | 8.24E-01 | 0.40% | 2.93 | 0.14% |
| AF555 (Mouse IgG1,k) | 4.68E-03 | 155% | - | - |
| AF647 (Mouse IgG2a,k) | 8.16E-03 | 91.5% | 4.9 | 18.7% |
| BV480 (Goat Ig) | 6.98E-01 | 0.56% | 2.96 | 0.19% |
| PE (Mouse IgG2a,k) | 3.88E-01 | 1.88% | 1.09 | 1.72% |
| BV605 (Mouse IgG1,k) | 2.53E-01 | 1.96% | 3.68 | 0.53% |
| PerCP-Cy5.5 (Mouse IgG1,k) | 1.95E-02 | 57.7% | 4.78 | 12.1% |
| PE-Cy7 (Rat IgG1,k) | 6.42E-02 | 3.18% | 0.92 | 3.46% |

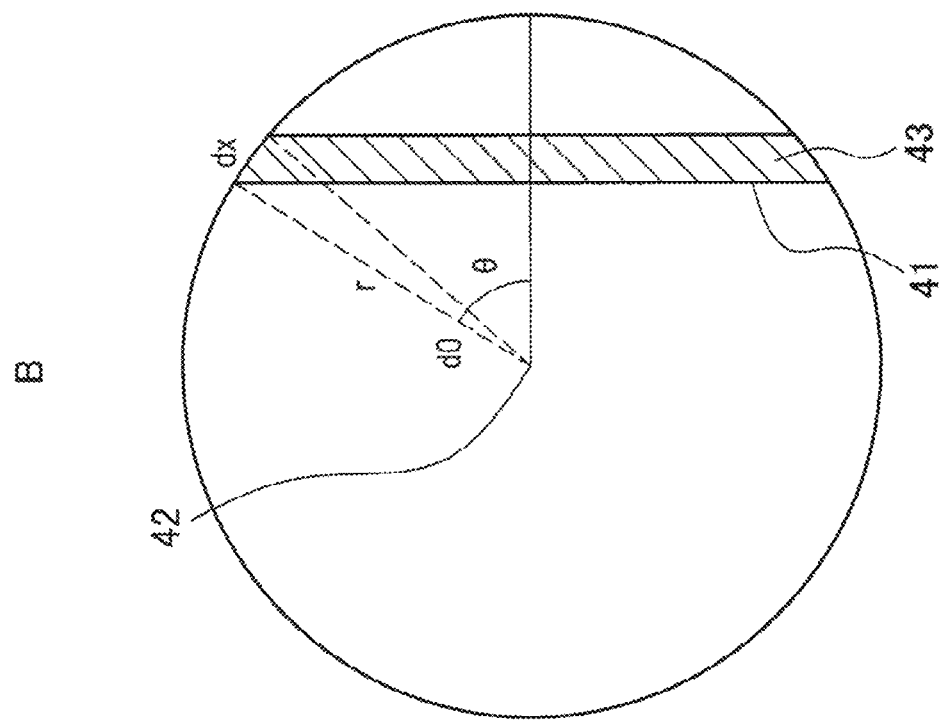
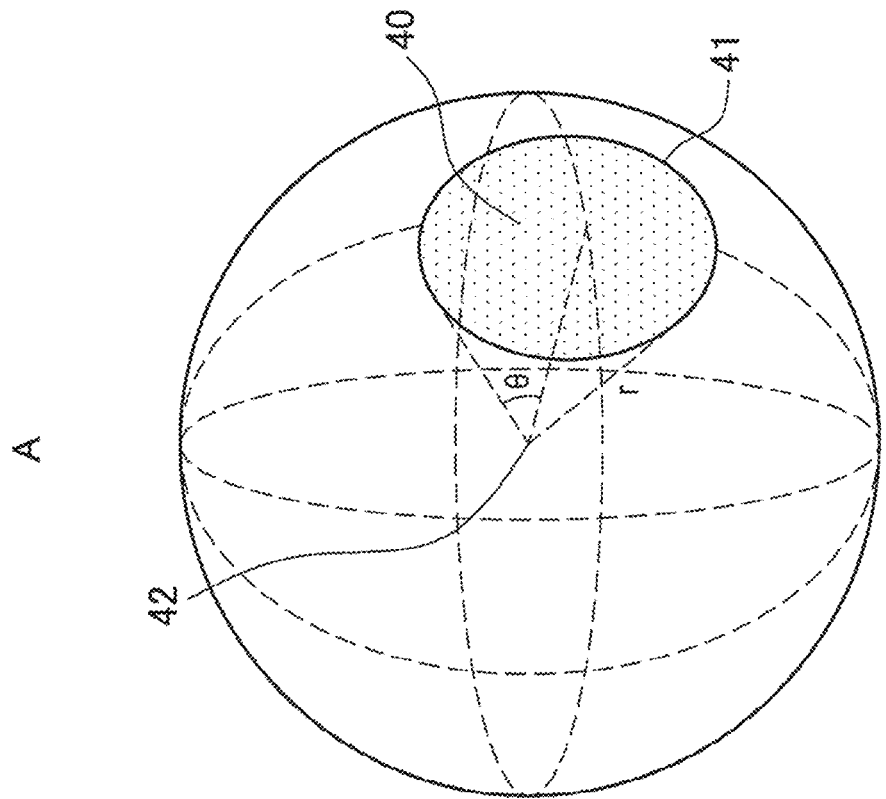
FIG.19

INFORMATION PROCESSING APPARATUS, INFORMATION PROCESSING METHOD, INFORMATION PROCESSING SYSTEM, AND COMPUTER PROGRAM

CROSS-REFERENCE TO RELATED APPLICATIONS

The present application claims the benefit under 35 U.S.C. § 120 as a continuation application of U.S. application Ser. No. 17/260,964, filed on Jan. 15, 2021, now U.S. Pat. No. 11,579,090, which claims the benefit under 35 U.S.C. § 371 as a U.S. National Stage Entry of International Application No. PCT/JP2019/026916, filed in the Japanese Patent Office as a Receiving Office on Jul. 5, 2019, which claims priority to Japanese Patent Application Numbers JP2019-005402, filed in the Japanese Patent Office on Jan. 16, 2019; and JP2018-138663, filed in the Japanese Patent Office on Jul. 24, 2018, each of which is hereby incorporated by reference in its entirety.

FIELD

The present disclosure relates to an information processing apparatus, an information processing method, an information processing system, and a computer program.

BACKGROUND

Having been conventionally known is a fluorescence microscope capable of generating fluorescence by irradiating an object to be observed that is dyed with a fluorescent dye reagent, with an excitation ray, of capturing an image of the fluorescence, and of outputting the resultant captured image information. In relation to the fluorescence microscope, because the brightness of the object to be observed is low compared with that in an ordinary microscope (brightfield microscope) for visible light, it is necessary to expose the imaging device to the excitation ray for a long time period, and the noise is likely to become included in the captured image information as a result of the extended exposure. Therefore, various technologies have been developed to remove the noise from the captured image information of the fluorescence.

For example, Patent Literature 1 listed below discloses a technology capable of removing noise more appropriately when tiling is applied to an image of an object to be observed that is dyed with a fluorescent dye reagent (when the image is divided into tiles), using a fluorescence microscope.

CITATION LIST

Patent Literature

Patent Literature 1: JP 2013-25466 A

SUMMARY

Technical Problem

However, in the technology disclosed in Patent Literature 1, the effect of fading of the fluorescence of the fluorescent substance is not appropriately taken into consideration. To explain more specifically, it has been known that, when a fluorescent substance is irradiated with an excitation ray, the fluorescence intensity of the fluorescent substance drops (that is, fluorescence fading occurs or its apparent quantum yield drops) depending on the intensity of the excitation ray and the passage of the irradiation time. Therefore, depending on technologies such as that disclosed in Patent Literature 1, observers sometimes fail to evaluate information corresponding to fluorescent molecules (for example, the number of fluorescent molecules or the number of antibodies bounded to fluorescent molecules) appropriately, using the captured image information of the fluorescence.

To address this issue, the present disclosure is made in consideration of the above problem, and an object of the present disclosure is to provide a novel and improved information processing apparatus, information processing method, information processing system, and computer program capable of calculating information corresponding to fluorescent molecules, while taking the effect of fluorescence fading of the fluorescent substance into consideration.

Solution to Problem

According to the present disclosure, an information processing apparatus is provided that includes: an image acquiring unit that acquires captured image information of a sample dyed with a fluorescent dye reagent; an information acquiring unit that acquires information related to the fluorescent dye reagent; a correcting unit that corrects luminance of the captured image information using a fluorescence fading coefficient that represents rapidness at which a fluorescence intensity of the fluorescent dye reagent drops, the fluorescence fading coefficient being included in the information related to the fluorescent dye reagent; and a calculating unit that calculates information corresponding to fluorescent molecules in the captured image information, using the corrected luminance.

Moreover, according to the present disclosure, an information processing method executed by a computer is provided that includes: acquiring captured image information of a sample dyed with a fluorescent dye reagent; acquiring information related to the fluorescent dye reagent; correcting luminance of the captured image information using a fluorescence fading coefficient that represents rapidness at which a fluorescence intensity of the fluorescent dye reagent drops, the fluorescence fading coefficient being included in the information related to the fluorescent dye reagent; and calculating information corresponding to fluorescent molecules in the captured image information, using the corrected luminance.

Moreover, according to the present disclosure, a computer program is provided that causes a computer to execute: acquiring captured image information of a sample dyed with a fluorescent dye reagent; acquiring information related to the fluorescent dye reagent; correcting luminance of the captured image information using a fluorescence fading coefficient that represents rapidness at which a fluorescence intensity of the fluorescent dye reagent drops, the fluorescence fading coefficient being included in the information related to the fluorescent dye reagent; and calculating information corresponding to fluorescent molecules in the captured image information, using the corrected luminance.

Moreover, according to the present disclosure, an information processing system is provided that includes: an image acquiring unit that acquires captured image information of a sample dyed with a fluorescent dye reagent; an information acquiring unit that acquires information related to the fluorescent dye reagent; a correcting unit that corrects luminance of the captured image information using a fluorescence fading coefficient that represents rapidness at which a fluorescence intensity of the fluorescent dye reagent drops, the fluorescence fading coefficient being included in the information related to the fluorescent dye reagent; a calculating unit that calculates information corresponding to fluorescent molecules in the captured image information, using the corrected luminance; and a display unit that displays image information generated based on the information corresponding to fluorescent molecules.

Advantageous Effects of Invention

According to the present disclosure as explained above, it becomes possible to calculate information corresponding to fluorescent molecules, while taking the effect of fluorescence fading of the fluorescent substance into consideration.

The effect described above is not necessarily limiting, and any of the effects described herein or other effects understood from the description herein may be achieved, in addition to, or instead of the effect described above.

BRIEF DESCRIPTION OF DRAWINGS

FIG. 9 is a schematic illustrating results of comparisons between actual measurements of and catalog specifications of quantum yields.

FIG. 12 is a schematic illustrating captured image information applied with a fluorescence fading correction, and represented in a 16-[bit] gradation.

FIG. 13 is a schematic illustrating image information generated by converting the luminance of each pixel into the number of fluorescent molecules, and represented in a 10-[bit] gradation.

FIG. 14 is a schematic illustrating image information generated by converting the luminance of each pixel into the number of antibodies, and represented in an 8-[bit] gradation.

FIG. 15 is a schematic illustrating actual measurements of the number of photons per one molecule, an image compression ratio representing the number of fluorescent molecules, a fluorescent labeling ratio, and an image compression ratio representing the number of antibodies, all of which are actually measured for each of the fluorescent substances.

FIG. 19 is a schematic for explaining a method for deriving a ratio (Equation 14) of the range detectable through the objective lens, with respect to the full range about the radiant point 42 of the fluorescence.

DESCRIPTION OF EMBODIMENTS

Figure 1:
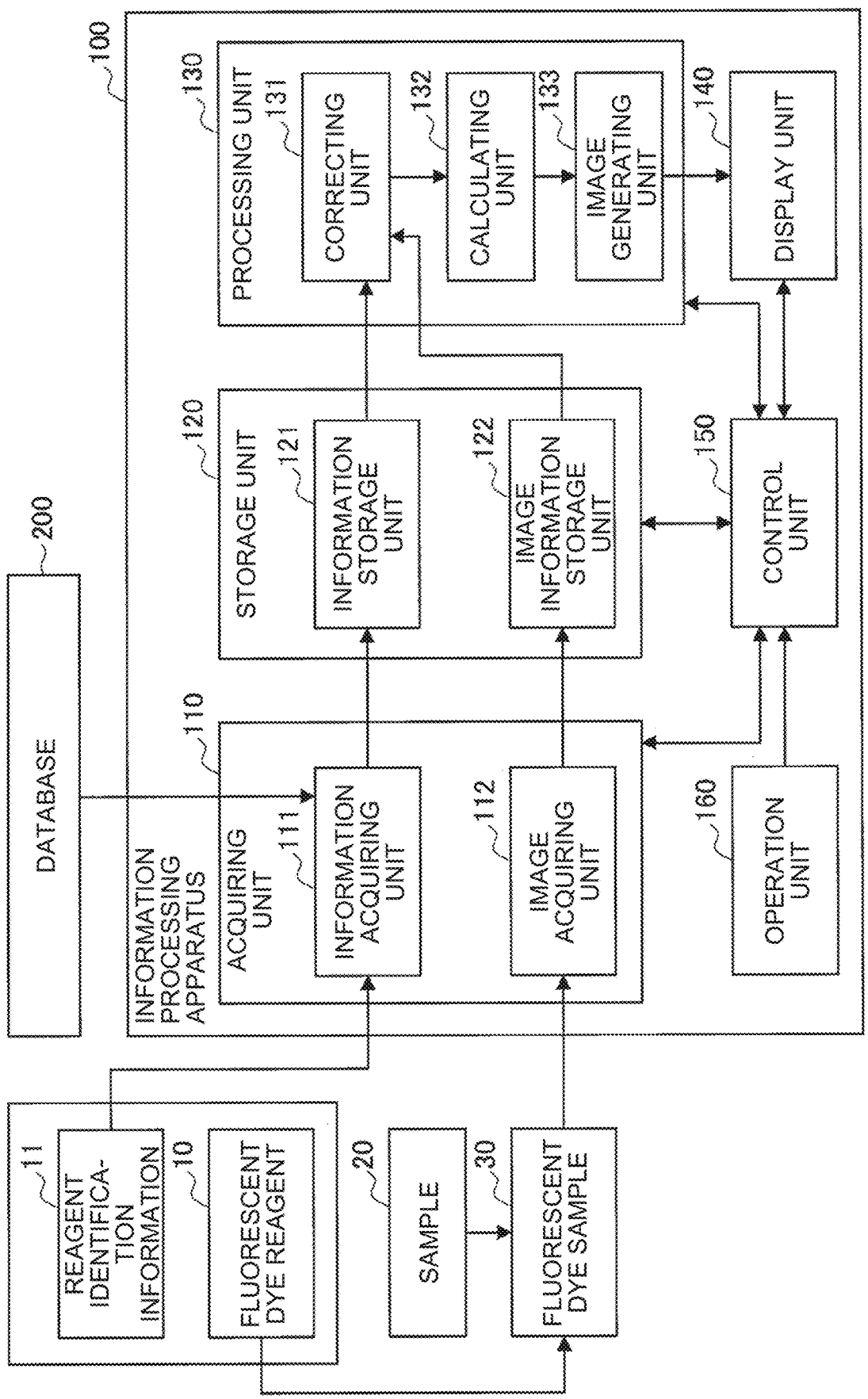
FIG. 1 is a block diagram illustrating an exemplary configuration of an information processing system according to an embodiment.

A preferred embodiment according to the present disclosure will now be explained in detail with reference to the appended drawings. In the specification and the drawings, the elements having substantially the same functional configurations will be given the same reference signs, and redundant explanations thereof will be omitted.

The explanation will be provided in the following order.
1. Overview
2. Exemplary Configuration
3. Example of Sequence of Process
4. Embodiment
5. Correction Related to Fluorescence Saturation
6. Exemplary Hardware Configuration
7. Remarks
8. Summary 1. Overview An overview of the present disclosure will now be provided.

As described earlier, it has been known that, when a fluorescent substance is irradiated with an excitation ray, the fluorescence intensity of the fluorescent substance drops (that is, that fluorescence fading occurs, or the apparent quantum yield drops) depending on the intensity of the excitation ray and the passage of the irradiation time. In the technology disclosed in Patent Literature 1, the effect of fluorescence fading of the fluorescent substance has not been appropriately taken into consideration. The rapidness at which the fluorescence fading of the fluorescent substance takes place differs greatly depending on the fluorescent substance, and there are some fluorescent substances that keep emitting fluorescence for a long time, and there are others having fluorescence that fades instantaneously, even if the excitation ray at the same intensity is used. Because of this difference, it has been sometimes impossible for an observer to evaluate information corresponding to fluorescent molecules (e.g., the number of fluorescent molecules or the number of antibodies bounded to fluorescent molecules). In particular, when an observer compares the number of fluorescent molecules among a plurality of fluorescent substances, quantitative comparisons have been sometimes difficult.

In consideration of the above, the inventor of the present disclosure has come to create a technology according to the present disclosure. An information processing apparatus 100 according to the present disclosure acquires captured image information of a sample dyed with a fluorescent dye reagent, acquires information related to the fluorescent dye reagent, and corrects the luminance of the captured image information using a fluorescence fading coefficient representing the rapidness at which the fluorescence intensity of the fluorescent dye reagent drops, the fluorescence fading coefficient being included in the information related to the fluorescent dye reagent. The information processing apparatus 100 can then calculate information corresponding to the fluorescent molecules (e.g., the number of fluorescent molecules or the number of antibodies bonded to fluorescent molecules), in the captured image information, using the corrected luminance, and output image information reflected with the information. The "information related to the fluorescent dye reagent" (hereinafter, referred to as "reagent information", for the purpose of convenience) may include, in addition to the fluorescence fading coefficient, a quantum yield, an absorption cross section (or a molar absorbance coefficient), and a fluorescent labeling ratio that are related to the fluorescent dye reagent. However, the information included in the reagent information is not limited thereto.

In other words, by converting the luminance of the captured image information into the number of fluorescent molecules, for example, the information processing apparatus 100 can output the image information reflected with the number of fluorescent molecules. With this, the information processing apparatus 100 can implement a quantitative evaluation without the dependency on the measurement conditions or the characteristics of the fluorescent substances. For example, even if the type of the fluorescent substance to be used (fluorescence labeling type) is changed, the information processing apparatus 100 can output substantially the same number of fluorescent molecules even before and after the fluorescent substance is changed. Furthermore, the information processing apparatus 100 can compare the number of fluorescent molecules (or the number of antibodies bonded to fluorescent molecules) among a plurality of fluorescent substances, more appropriately.

Furthermore, in a measurement of the number of fluorescent molecules, fluorescent dye samples may be irradiated with an excitation ray at a higher intensity so that a higher fluorescence signal is generated. In such a case, because, when the intensity of the excitation ray becomes higher, the speed of the fluorescence fading, too, becomes higher, fluorescence fading may start to take place before the image is captured, and it might not be possible to acquire appropriate captured image information. By contrast, because the information processing apparatus 100 can correct the luminance of the captured image information using a fluorescence fading coefficient (hereinafter, "the correction of the luminance of the captured image information, performed using a fluorescence fading coefficient" will be referred to as a "fluorescence fading correction"), even when a high-intensity excitation ray is to be used, it is possible to acquire appropriate captured image information. In other words, by performing the fluorescence fading correction, the information processing apparatus 100 can acquire captured image information in a shorter time period by increasing the intensity of the excitation ray.

Furthermore, as mentioned earlier, because the information processing apparatus 100 can output image information based on the number of fluorescent molecules (or the number of antibodies bonded to fluorescent molecules), it is possible to adjust the gradation of the image information depending on the number of fluorescent molecules, for example. In this manner, the information processing apparatus 100 can optimize the quality and the amount of data of the image information (or can bring the quality and the amount of data closer to the optimal). While the fluorescence intensity of the fluorescent substance or the luminance of the captured image information is a continuous value, the number of fluorescent molecules or the number of antibodies is a discrete value. Therefore, the information processing apparatus 100 can reduce the amount of data by outputting the image information based on the number of fluorescent molecules or the number of antibodies.

In the embodiment according to the present disclosure, it is assumed that the fluorescence fading coefficient is measured separately using different samples from those used in the measurement of the number of fluorescent molecules (or the number of antibodies bonded to fluorescent molecules). For example, when the measurement of the number of fluorescent molecules or the like and the measurement of the fluorescence fading coefficient are to be performed at once, a measurement environment at a high-time resolution is required (particularly for a fluorescent substance in which fluorescence fading takes place quickly). By contrast, when the fluorescence fading coefficient is to be measured separately, as is in the embodiment according to the present disclosure, by irradiating a high-concentration fluorescent substance with a low-intensity excitation ray, it becomes possible to measure a more precise fluorescence fading coefficient even in a measurement environment where the time resolution is relatively low. Because the signal-noise (SN) ratio is improved more when the luminance of the captured image information is higher, the fluorescence fading coefficient is calculated more accurately.

Furthermore, when measurements of the number of fluorescent molecules or the like and of the fluorescence fading coefficient are performed at once, sometimes the luminance of the captured image information becomes insufficient, and it sometimes becomes impossible to calculate a fluorescence fading coefficient appropriately. By contrast, when the fluorescence fading coefficient is calculated separately, as in the embodiment according to the present disclosure, the fluorescence fading coefficient can be calculated more reliably.

Furthermore, when the measurement of the number of fluorescent molecules or the like and the measurement of the fluorescence fading coefficient are performed at once, there is a possibility that the luminance originating from a substance other than the fluorescent dye reagent, e.g., that originating from autofluorescence of tissues or cells, might be acquired simultaneously with the luminance of the target luminance. As a result, the accuracy of the fluorescence fading coefficient calculation may drop, and it might become necessary to correct the luminance of the captured image information. By contrast, when the fluorescence fading coefficient is measured separately, as in the embodiment according to the present disclosure, because it is possible to acquire the luminance only corresponding to the fluorescence emitted from the target fluorescent substance, it is possible to calculate the fluorescence fading coefficient more accurately.

This approach for measuring the fluorescence fading coefficient and the number of fluorescent molecules or the like separately is merely one example. In other words, the fluorescence fading coefficient and the number of fluorescent molecules or the like may also be measured at once.

2. Exemplary Configuration

The overview of the present disclosure has been explained above. An exemplary configuration of an information processing system according to one embodiment of the present disclosure will now be explained with reference to FIG. 1.

As illustrated in FIG. 1, the information processing system according to the embodiment includes the information processing apparatus 100 and a database 200, and there are a fluorescent dye reagent 10, a sample 20, and a fluorescent dye sample 30, as the inputs to the information processing system.

(Fluorescent Dye Reagent 10)

The fluorescent dye reagent 10 is a chemical that is used to dye the sample 20. Examples of the fluorescent dye reagent 10 include a fluorescent antibody, a fluorescent probe, and a nuclear staining reagent, but the type of the fluorescent dye reagent 10 is not limited to any particular type. Furthermore, the fluorescent dye reagent 10 is managed in a manner appended with identification information (hereinafter, referred to as "reagent identification information 11") capable of identifying the fluorescent dye reagent 10 (and the production lot of the fluorescent dye reagent 10). The reagent identification information 11 is barcode information (such as one-dimensional barcode information or two-dimensional barcode information), for example, but is not limited to the barcode information. Even if the fluorescent dye reagent 10 is the same product (the same type), the characteristics of the fluorescent dye reagent 10 become different among the production lots, depending on the manufacturing method or the cells from which the antibodies are acquired. For example, the fluorescent dye reagent 10 has a different fluorescence fading coefficient or fluorescent labeling ratio (also referred to as a "fluorescein/protein (F/P) value", which represents the number of fluorescent molecules for labeling antibodies). Therefore, in the information processing system according to the embodiment, the fluorescent dye reagent 10 is managed by production lot, by assigning the reagent identification information 11 (in other words, the reagent information of the fluorescent dye reagent 10 is managed by production lot). In this manner, the information processing apparatus 100 can perform various processes by taking a slight difference in the characteristics unique to the production lot into consideration. This management of the fluorescent dye reagent 10 by production lot is merely one example, and the fluorescent dye reagent 10 may be managed in a unit smaller than a production lot.

(Sample 20)

The sample 20 is fabricated from specimens or tissue samples that are derived from human bodies, for a purpose such as a pathological diagnosis. In relation to the sample 20, the type of bodily tissues to be used (such as an organ), the type of the target disease, the attribute of the subject (e.g., age, sex, blood type, or race), or the lifestyle habit of the subject (e.g., diet, exercise habit, or smoking habit) are not limited to any particular ones. Because the sample 20 exhibits different characteristics depending on the type of bodily tissues to be used, the type of the target disease, the attribute of the subject, the lifestyle habit of the subject, and the like, the sample 20 may be managed in a manner appended with identification information capable of identifying each sample 20.

(Fluorescent Dye Sample 30)

The fluorescent dye sample 30 is made by dying the sample 20 with the fluorescent dye reagent 10. In this embodiment, it is assumed that the fluorescent dye sample 30 is achieved by dying the sample 20 using at least one fluorescent dye reagent 10, but the number of fluorescent dye reagents 10 to be used in dying are not limited to any particular number. Furthermore, the dying method is determined based on a combination of the sample 20 and the fluorescent dye reagent 10, for example, and is not limited to any particular method. The fluorescent dye sample 30 is input to, and has their image captured by the information processing apparatus 100.

(Information Processing Apparatus 100)

The information processing apparatus 100 includes, as illustrated in FIG. 1, an acquiring unit 110, a storage unit 120, a processing unit 130, a display unit 140, a control unit 150, and an operation unit 160.

(Acquiring Unit 110)

The acquiring unit 110 is a configuration for acquiring information used in various processes performed by the information processing apparatus 100. As illustrated in FIG. 1, the acquiring unit 110 includes an information acquiring unit 111 and an image acquiring unit 112.

(Information Acquiring Unit 111)

The information acquiring unit 111 is a configuration for acquiring various types of information such as the reagent information. More specifically, the information acquiring unit 111 acquires the reagent identification information 11 appended to the fluorescent dye reagent 10 used in creating the fluorescent dye sample 30. For example, the information acquiring unit 111 acquires the reagent identification information 11 using a barcode reader, for example. The information acquiring unit 111 acquires the reagent information from the database 200, based on the reagent identification information 11. The information acquiring unit 111 also acquires an actual measurement of the excitation power density that is measured separately (a subject for measuring the excitation power density is not limited to any particular subject). The information acquired by the information acquiring unit 111 is not limited thereto. The information acquiring unit 111 stores these pieces of acquired information in a information storage unit 121, which will be described later.

(Image Acquiring Unit 112)

The image acquiring unit 112 is a configuration that acquires captured image information of the fluorescent dye sample 30 (the sample 20 dyed with the fluorescent dye reagent 10). More specifically, the image acquiring unit 112 is provided with an imaging device (e.g., a charge-coupled device (CCD) or a complementary metal oxide semiconductor (CMOS)), and acquires captured image information by capturing an image of the fluorescent dye sample 30 using the imaging device. The "captured image information" is a concept that includes not only the captured image of the fluorescent dye sample 30 itself but also a measurement and the like that are not visualized as an image (e.g., a measurement of the luminance). The image acquiring unit 112 stores the captured image information in an image information storage unit 122, which will be described later.

(Storage Unit 120)

The storage unit 120 is a configuration that stores therein information (keeping the information in a memory) used in various processes performed by the information processing apparatus 100, and information output from the various processes. As illustrated in FIG. 1, the storage unit 120 includes an information storage unit 121 and an image information storage unit 122.

(Information Storage Unit 121)

The information storage unit 121 is a configuration that stores therein various types of information such as the reagent information acquired by the information acquiring unit 111 (e.g., the fluorescence fading coefficient, the absorption cross section (or the molar absorbance coefficient), the quantum yield, and the fluorescent labeling ratio, as mentioned earlier). After processes such as a fluorescence fading correcting process performed by the correcting unit 131, a process of calculating the number of fluorescent molecules (or the number of antibodies bonded to fluorescent molecules) performed by the calculating unit 132, or an image generating process performed by an image generating unit 133, which are to be described later, the information storage unit 121 may delete these pieces of information used in these process so that the available capacity is increased.

(Image Information Storage Unit 122)

The image information storage unit 122 is a configuration that stores therein captured image information of the fluorescent dye sample 30 (keeping the information in a memory) acquired by the image acquiring unit 112. In the same manner as the information storage unit 121, after processes such as the fluorescence fading correcting process performed by the correcting unit 131, the process of calculating the number of fluorescent molecules (or the number of antibodies bonded to fluorescent molecules) performed by the calculating unit 132, or the image generating process performed by the image generating unit 133, the image information storage unit 122 may delete the captured image information used in the processes so that the available capacity is increased.

(Processing Unit 130)

The processing unit 130 is a functional configuration that performs various processes using the information such as the captured image information, the reagent information (e.g., the fluorescence fading coefficient, the absorption cross section (or the molar absorbance coefficient), the quantum yield, and the fluorescent labeling ratio, as mentioned earlier), and the excitation power density. As illustrated in FIG. 1, the processing unit 130 includes a correcting unit 131, a calculating unit 132, and an image generating unit 133.

(Correcting Unit 131)

The correcting unit 131 is a configuration that performs a fluorescence fading correcting process to the captured image information. More specifically, the correcting unit 131 corrects the luminance of the captured image information to that before fluorescence fading has taken place, using the fluorescence fading coefficient, the absorption cross section, the excitation power density, and the like. The fluorescence fading correcting process performed by the correcting unit 131 will be explained in detail in a later section.

(Calculating Unit 132)

The calculating unit 132 is a configuration that calculates information corresponding to the fluorescent molecules (such as the number of fluorescent molecules or the number of antibodies) in the captured image information, using the luminance of the captured image information, the luminance being corrected by the correcting unit 131. More specifically, the calculating unit 132 converts the luminance of each of the corrected pixels into the number of fluorescent molecules or the number of antibodies, using the absorption cross section, the quantum yield, the fluorescent labeling ratio, and the excitation power density, for example. The process of calculating the number of fluorescent molecules or the number of antibodies, performed by the calculating unit 132, will be explained in detail in a later section.

In this embodiment, it is assumed that calculations of the fluorescence fading coefficient, the quantum yield, and the like of the fluorescent substance is performed separately from the calculation of the number of fluorescent molecules or the like (of course, without limitation thereto). At that time, the calculating unit 132 can implement the process of calculating the fluorescence fading coefficient, the quantum yield, and the like.

(Image Generating Unit 133)

The image generating unit 133 is a configuration that generates image information based on the information corresponding to the fluorescent molecules (such as the number of fluorescent molecules or the number of antibodies), calculated by the calculating unit 132. The "image information" is a concept that includes not only the image itself but also numbers or the like not visualized as an image (such as the number of fluorescent molecules or the number of antibodies), in the same manner as in the captured image information explained above. The process of generating the image information performed by the image generating unit 133 will be explained in detail in a later section.

(Display Unit 140)

The display unit 140 is a configuration that presents the image information generated by the image generating unit 133 (the image information generated based on the information corresponding to the fluorescent molecules) to the user, by displaying the image information on a display. The type of the display used as the display unit 140 is not limited to any particular type. Although no detailed explanation is provided in this embodiment, the image information generated by the image generating unit 133 may be presented to the user by projecting the image information with a projector, or by printing the image information with a printer (in other words, the way in which the image information is output is not limited to any particular way).

(Control Unit 150)

The control unit 150 is a configuration that controls the entire processes performed by the information processing apparatus 100 comprehensively. For example, the control unit 150 controls to start and to end various processes such as those explained above (e.g., the process of capturing an image of the fluorescent dye sample 30, the process of correcting the fluorescence fading, the process of calculating the number of fluorescent molecules (or the number of antibodies bonded to fluorescent molecules), the process of generating the image information, and the process of displaying the image information), based on an operation input performed by a user via the operation unit 160. The control performed by the control unit 150 is not limited to that of the processes described above. For example, the control unit 150 may also control processes that are generally performed in a general-purpose computer, a personal computers (PC), or a tablet PC (e.g., processes related to an operating system (OS)).

(Operation Unit 160)

The operation unit 160 is a configuration that receives operation inputs from a user. More specifically, the operation unit 160 includes various input units such as a keyboard, a mouse, a button, a touch panel, or a microphone, and the user can enter various inputs to the information processing apparatus 100 by making operations on these input units. The information related to the operation inputs performed via the operation unit 160 is provided to the control unit 150.

(Database 200)

The database 200 is a device that manages information related to the fluorescent dye reagent 10, e.g., the fluorescence fading coefficient, the absorption cross section (or the molar absorbance coefficient), the quantum yield, and the fluorescent labeling ratio. To explain more specifically, the database 200 manages the reagent identification information 11 in a manner associated with information such as the fluorescence fading coefficient, the absorption cross section (or the molar absorbance coefficient), the quantum yield, and the fluorescent labeling ratio. With this association, the information acquiring unit 111 can acquire these pieces of information from the database 200, based on the reagent identification information 11 of the fluorescent dye reagent 10. The database 200 may also manage various types of information related to the sample 20, using identification information capable of identifying the sample 20. Furthermore, the database 200 may also manage other information including an actual measurement of the excitation power density, for example.

An exemplary configuration of the information processing system according to the embodiment has been explained above. The configuration explained above with reference to FIG. 1 is merely one example, and the information processing system according to the embodiment is not limited to the example described above. For example, it is not necessarily needed for the information processing apparatus 100 to be provided with all of the configurations illustrated in FIG. 1. The configuration of the information processing apparatus 100 may be modified flexibly depending on the specifications or on the operation.

3. Example of Sequence of Process

An exemplary configuration of the information processing system according to the embodiment has been explained above. An example of the sequence of a process performed in the information processing system according to the embodiment will now be explained.

3.1. Example of Entire Sequence of Process of Calculating Number of Fluorescent Molecules An example of the entire sequence of a process of calculating the number of fluorescent molecules (or the number of antibodies bonded to fluorescent molecules) will now be explained with reference to FIG. 2.

At Step S1000, a user determines the fluorescent dye reagent 10 and the sample 20 to be used in an analysis. At Step S1004, the user then prepares the fluorescent dye sample 30 by dying the sample 20 using the fluorescent dye reagent 10.

At Step S1008, the image acquiring unit 112 in the information processing apparatus 100 acquires captured image information by capturing an image of the fluorescent dye sample 30. At Step S1012, the information acquiring unit 111 acquires the reagent information such as the fluorescence fading coefficient, the absorption cross section, the quantum yield, and the fluorescent labeling ratio, from the database 200, based on the reagent identification information 11 appended to the fluorescent dye reagent 10 used in generating the fluorescent dye sample 30. The information acquiring unit 111 also separately acquires an actual measurement of the excitation power density.

At Step S1016, the correcting unit 131 corrects the luminance of each pixel in the captured image information, using the fluorescence fading coefficient, the absorption cross section, the excitation power density, and the like (performs the fluorescence fading correcting process). At Step S1020, the calculating unit 132 converts the corrected luminance at each pixel into the number of photons. At Step S1024, the calculating unit 132 converts the number of photons into the number of fluorescent molecules or the number of antibodies bonded to fluorescent molecules.

At Step S1028, the image generating unit 133 generates image information reflected with the number of fluorescent molecules or the number of antibodies bonded to fluorescent molecules. At Step S1032, the display unit 140 displays the image information on the display, and the sequence of the processes is ended.

3.2. Fluorescence Fading Correcting Process

The fluorescence fading correcting process at Step S1016 illustrated in FIG. 2 will now be explained in detail.

Equation 1 indicated below is a type of a model representing the fluorescence fading characteristic of a fluorescent substance. To explain more specifically, Equation 1 indicated below is an equation representing the fluorescence fading coefficient φ of the fluorescent substance, defined as the number of photons absorbed by the fluorescent substance, or a probability at which the fluorescent substance goes through fluorescence fading per excitation power density.

$$F = F_0 \times \mathrm{Exp}\{-(\text{Abs photon}) \times \phi \times t\} \quad (1)$$

Figure 3:
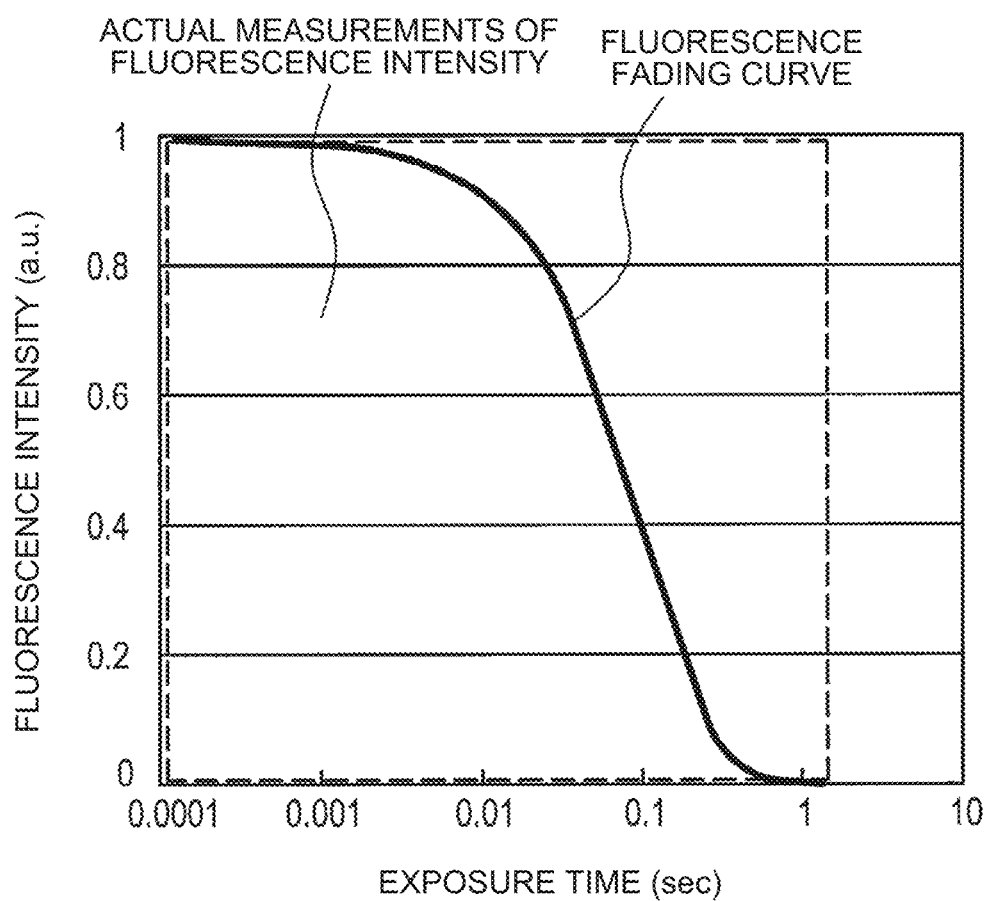
FIG. 3 is a schematic for explaining a fluorescence fading correcting process.

F: Fluorescence Intensity After Fluorescence Fading
$F_0$: Initial Value (Fluorescence Intensity Before Fluorescence Fading)
Abs photon: Number of Absorbed Photons (Number of Photons Absorbed by One Fluorescent Dye Molecule per Second)
φ: Fluorescence Fading Coefficient
t: Exposure Time The actual measurement of the fluorescence intensity is expressed by Equation 2 indicated below, as an integral of Equation 1. The "actual measurement of the fluorescence intensity" means the fluorescence intensity acquired during the period of exposure, and is equal to the area surrounded by the fluorescence fading curve illustrated in FIG. 3.

$$\text{Actual Measurement of Fluorescence Intensity} = F_0 \times \left\{ \frac{1 - \mathrm{Exp}(-(\text{Abs photon}) \times \phi \times t)}{(\text{Abs photon}) \times \phi} \right\} \quad (2)$$

The initial value $F_0$ of the fluorescence intensity is expressed as Equation 3 indicated below, based on Equation 2, and the correcting unit 131 outputs the fluorescence intensity after the fluorescence fading correcting process, as Equation 4 indicated below, by multiplying the exposure time t to the initial value $F_0$. The fluorescence intensity after the fluorescence fading correcting process is equal to the area surrounded by a dotted line in FIG. 3.

$$F_0 = \text{Actual Measurement of Fluorescence Intensity} / \left\{ \frac{1 - \mathrm{Exp}(-(\text{Abs photon}) \times \phi \times t)}{(\text{Abs photon}) \times \phi} \right\} \quad (3)$$

Fluorescence Intensity After Fluorescence Fading
Correction = $F_0 \times t$ \quad (4)

Where the number of absorbed photons (Abs photon) is expressed by Equations 5 to 7 indicated below.

$$(\text{Abs photon}) = \text{Excited Photon Density} \times \text{Absorption Cross Section} \quad (5)$$

$$\text{Excited Photon Density} = \frac{\text{Excitation Power Density}}{\text{Energy of One [photon]}} \quad (6)$$

$$\text{Energy of One [photon]} = \frac{h \times c}{\lambda} \approx 3.66 \times 10^{-19} [J] \quad (7)$$

h: Planck Constant ($6.62607 \times 10^{-34}$ [Js])
c: Light Speed in Vacuum ($2.99792458 \times 10^8$ [m/s])
λ: Wavelength of Electromagnetic Wave in Vacuum (In This Embodiment, $543 \times 10^{-9}$ [m] As One Example)

The excitation power density used in the calculation of the excitation photon density in Equation 6 is actually measured in this embodiment, and is managed in the database 200. The subject that measures the excitation power density is not limited to any particular subject. In this embodiment as an example, the calculating unit 132 collects the actual measurement of the excitation power density. For example, by providing an aperture on the light path of the illumination light source, and by emitting an excitation ray with a small aperture opening, the calculating unit 132 can measure the power of the excitation ray with which a specific area is irradiated. The calculating unit 132 can measure the irradiated area, by analyzing captured image information with the aperture provided.

The method for measuring the irradiated area is not limited to any particular method. For example, the calculating unit 132 may analyze captured image information of an observation target sample being irradiated with an excitation ray (because the purpose is to measure the irradiated area, the observation target sample may be a sample containing only the mounting medium), using some image processing software, count the number of pixels irradiated with the excitation ray, and measure the irradiated area based on the number of pixels.

For example, it is assumed that the number of pixels within the area irradiated with the excitation ray is 354221 pixels. Supposing that one side of the pixel of an imaging device (such as a CMOS) is 3.45 [μm], and that the magnification power of the objective lens of the fluorescence microscope is 20 [times], one side of the square corresponding to one pixel on the surface of the observation target sample is expressed in Equation 8 indicated below, and the irradiated area is expressed as Equation 9 indicated below.

$$\frac{3.45[\mu m]}{20[\text{Times}]} = 0.1725[\mu m] \quad (8)$$

$$0.1725^2 \; [\mu m^2] \times 354221 [\text{Pixels}] \approx 1.05 \times 10^{-4} \; [cm^2] \quad (9)$$

When the energy emitted from the light source of the fluorescence microscope is measured to be 0.551 [mW] using a power meter, the excitation power density is expressed as Equation 10 indicated below based on the energy and the irradiated area. By calculating the excitation power density in the manner described above, the calculating unit 132 can calculate the excitation photon density in Equation 5 above.

$$\text{Excitation Power Density} \approx \frac{0.551[mW]}{1.05 \times 10^{-4}[cm^2]} \approx 5228[mW/cm^2] \quad (10)$$

The absorption cross section in Equation 5 above indicates the easiness at which a photon is absorbed per fluorescent dye molecule, and is expressed as Equation 11 indicated below, using the molar absorbance coefficient E [L/mol/cm]. In Equation 11, 1960000 [L/mol/cm] is used as the molar absorbance coefficient & that is a molar absorbance coefficient of phycoerythrin (PE), which is one kind of fluorescent substance, and the multiplication for 1 [L]=1000 [$cm^3$] is performed to convert [L] to [$cm^3$] to adjust to the unit of the excitation photon density. The division by 1 [mol]=$6.02 \times 10^{23}$ [molecules] is performed to convert into a value per fluorescent molecule. Because the absorbance is a log, 2.3 is multiplied to convert the log into Ln (ln(x)≈2.30 $\log_{10}(x)$). As described earlier, it is assumed that the absorption cross section is managed in the database 200 for each of the fluorescent dye reagents 10 (but the absorption cross section is not limited thereto, and the calculating unit 132 may calculate the absorption cross section every time the measurement is made).

$$\text{Absorption Cross Section} = \frac{1960000[L/mol/cm] \times 1000[cm^3] \times 2.3}{6.02 \times 10^{23}[\text{molecules}]} \approx 7.49 \times 10^{-15} [cm2/molecule] \quad (11)$$

The calculating unit 132 calculates the number of absorbed photons Abs photon by solving Equation 5 and Equation 6 above, using the values acquired as a result of the calculations above.

$$\text{Excited Photon Density} = \frac{\text{Excitation Power Density}}{\text{Energy of One Photon}} \approx \quad (6)$$

$$\frac{5.228[W/cm^2]}{3.66 \times 10^{-19}[J]} \approx 1.43 \times 10^{-19}[photon/s/cm^2]$$

(Abs photon)=Excited Photon Density×Absorption Cross Section ~$1.43 \times 10^{19}$ [photon/s/$cm^2$]×7.49× $10^{-15}$ [cm2/molecule]~$1.07 \times 10^5$ [photon/s/molecule] (5)

Because the calculating unit 132 can calculate the number of absorbed photons (Abs photon) through the process described above, the fluorescence fading correcting process can be implemented by solving Equation 3 and Equation 4 indicated above, using the number of absorbed photons (Abs photon), the fluorescence fading coefficient, and the exposure time.

3.3. Process of Converting Luminance into Number of Photons

A process of converting the luminance at each pixel into the number of photons, performed at Step S1020 in FIG. 2, will now be explained in detail.

The image acquiring unit 112 captures an image of a sample injected only with the mounting medium, as well as an image of the fluorescent dye sample 30, using an imaging device (e.g., a CMOS). The calculating unit 132 can then cancel the background noise attributable to the measurement system by subtracting the measurement result of the sample injected only with the mounting medium from the measurement result of the fluorescent dye sample 30, the measurement result having been applied with the fluorescence fading correcting process.

The calculating unit 132 can calculate the luminance at each pixel in the captured image information applied with the fluorescence fading correcting process, using some image processing software. Denoting one pixel as a pixel A, the calculating unit 132 calculates the number of electrons at the pixel A, using Equation 12 indicated below. It is assumed that the gradation of the captured image information is 16 [bits] (in other words, the luminance takes a value between 0 and 65536). In Equation 12, the luminance of the pixel A in the captured image information of the fluorescent dye sample 30, having been applied with the fluorescence fading correcting process, is indicated as "luminance 1", and the luminance of the pixel A in the captured image information of the sample injected only with the mounting medium is indicated as "luminance 2".

$$\text{Number of Electrons at Pixel } A[e-/s/\text{pixel}] = \qquad (12)$$
$$\frac{\text{Luminance 1} - \text{Luminance 2}}{65536[/\text{pixel}]} \times \text{Saturation Charge}$$
$$\text{of Imaging Device } [e-] \times \frac{1}{\text{Exposure Time }[s]}$$

The calculating unit 132 can calculate the number of photons at the pixel A by dividing the number of electrons at the pixel A by the quantum yield of the imaging device (e.g., a CMOS), as indicated in Equation 13 below.

$$\text{Number of Photons at Pixel } A[\text{photon}/s/\text{pixel}] = \qquad (13)$$
$$\frac{\text{Number of Electrons at Pixel } A}{\text{Quantum Yield of Imaging Device}}$$

Figure 4:
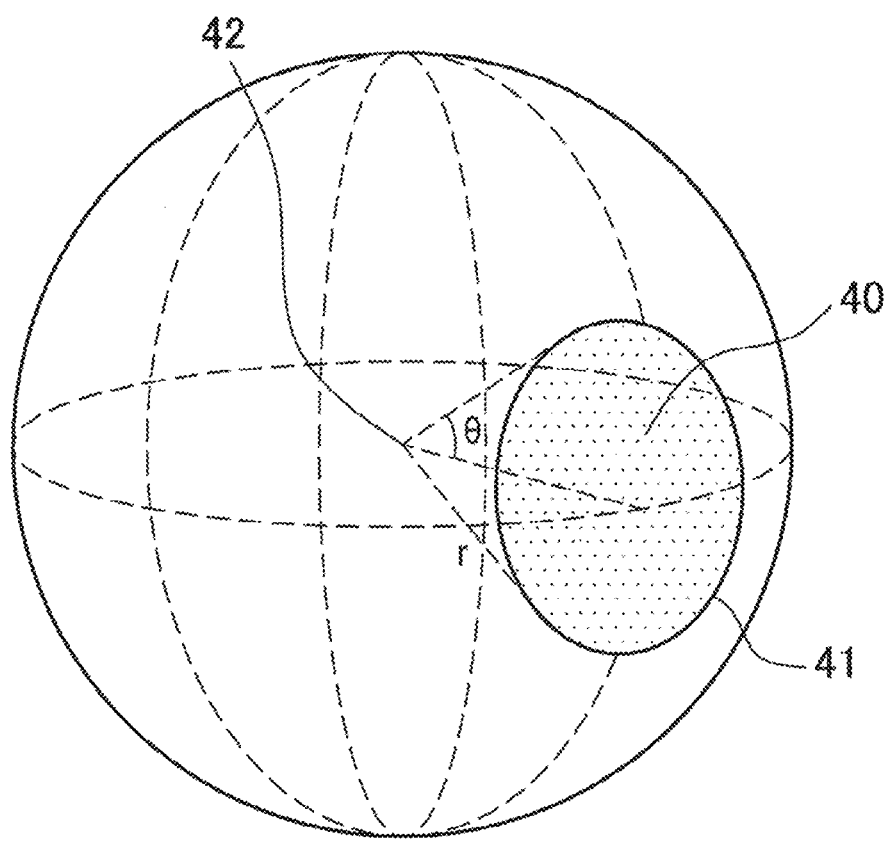
FIG. 4 is a schematic for explaining the range detectable through an objective lens of a fluorescence microscope.

While the luminance of the captured image information is a value related to the fluorescence detected through the objective lens of the fluorescence microscope, the fluorescent substance emits the fluorescence in the full range. As illustrated in FIG. 4, let us now consider an example in which a range 40 where the fluorescence is detectable through the objective lens is established as a conical part of a sphere that has the radiant point 42 of the fluorescence as its center, and a half apex angle of the cone is denoted as θ. The numerical aperture NA of the objective lens in the air is expressed as NA=sinθ. The ratio of the range 40 where fluorescence is detectable through the objective lens with respect to the full range about the radiant point 42 of the fluorescence is expressed as Equation 14 indicated below, using the numerical aperture NA of the objective lens. The full-range conversion of the number of photons detected at the pixel A is expressed as Equation 15 indicated below. The way in which Equation 14 is derived will be explained in detail in a later section.

$$\text{Ratio of Range Detectable Through Objective Lens,} \qquad (14)$$
$$\text{with Respect to Full Range} = \frac{1-\cos(\arcsin(NA))}{2}$$

$$\text{Number of Photons Detected at Pixel } A \text{ (Full - Range Conversion)} = \qquad (15)$$
$$\text{Number of Photons at Pixel } A / \frac{1-\cos(\arcsin(NA))}{2}$$

The calculating unit 132 converts the fluorescence intensity at each pixel into the number of photons by performing the process described above for all of the pixels including the pixel A.

3.4. Process of Converting Number of Photons into Number of Fluorescent Molecules or Number of Antibodies A process of converting the number of photons per pixel into the number of fluorescent molecules or the number of antibodies, performed at Step S1024 in FIG. 2, will now be explained in detail. To begin with, a process of converting the number of photons into the number of fluorescent molecules will be explained.

When the process of capturing an image of the fluorescent dye sample 30 is performed by an imaging device (e.g., a CMOS), the number of fluorescent molecules at a pixel A is expressed as Equation 16 and Equation 17 indicated below.

$$\text{Number of Fluorescent Molecules at Pixel } A = \qquad (16)$$
$$\frac{\text{Number of Photons Detected at Pixel } A(\text{Full-Range Conversion})}{\text{Number of Emitted Photons Per One Molecule}}$$

$$\text{Number of Emitted Photons Per One Molecule} = (\text{Abs photon}) \times \text{Quantum Yield of Fluorescent Substance} \qquad (17)$$

The calculating unit 132 calculates the number of emitted photons per molecule by inputting the Abs photon calculated in Equation 5, and the quantum yield of the fluorescent substance acquired from the database 200 to Equation 17. The calculating unit 132 then calculates the number of fluorescent molecules detected at the pixel A by inputting the number of photons detected at the pixel A (full-range conversion) calculated in Equation 15, and the number of emitted photons per molecule to Equation 16. The calculating unit 132 can convert the number of photons at each pixel into the number of fluorescent molecules, by performing the process described above for all of the pixels including the pixel A.

The calculating unit 132 can also convert the number of fluorescent molecules detected at the pixel A into the number of antibodies by performing the operation indicated in Equation 18 below, using fluorescent labeling ratio of the fluorescent substance, acquired from the database 200. The calculating unit 132 can calculate the number of antibodies per pixel by performing the operation indicated in Equation 18 to all of the pixels including the pixel A.

$$\text{Number of Antibodies at Pixel } A = \qquad (18)$$
$$\frac{\text{Number of Fluorescent Molecules at Pixel } A}{\text{Fluorescent Labeling Ratio}}$$

(3.5. Process of Generating Image Information)

The process of generating the image information reflected with the number of fluorescent molecules or the number of antibodies bonded to fluorescent molecules, performed at Step S1028 in FIG. 2, will now be explained.

Let us now assume that the calculating unit 132 has calculated the number of fluorescent molecules for all of the pixels, and the maximum number is M [molecules]. At this time, when the number of fluorescent molecules detected at a particular pixel is N [molecules], the image generating unit 133 calculates the luminance of the pixel as Equation 19 indicated below (the gradation of the image information is established as 16 [bits], as an example).

$$\text{Luminance of Pixel} = \frac{N}{M} \times 2^{16} \tag{19}$$

The image generating unit 133 generates the image information by performing the operation of Equation 19 for all of the pixels. In this manner, even when a plurality of fluorescent substances are used in dying, a user can compare the number of fluorescent molecules corresponding to the respective fluorescent substances by causing the image generating unit 133 to generate the image information reflected with the number of fluorescent molecules for each of the fluorescent substances by setting the maximum number of fluorescent molecules corresponding to the fluorescent substance as M [molecules].

3.6. Example of Sequence of Process of Measuring Fading Coefficient

Figure 2:
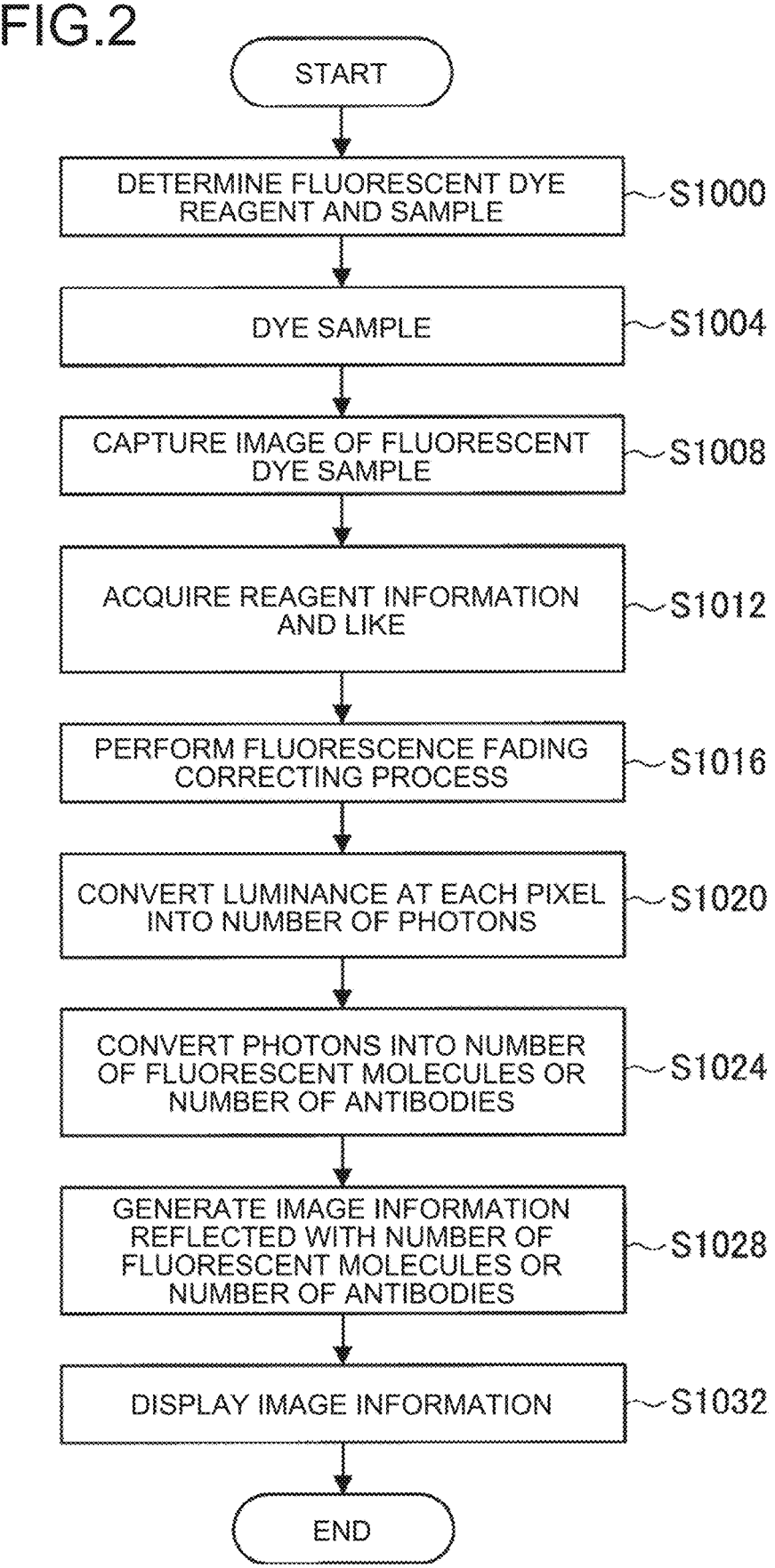
FIG. 2 is a flowchart illustrating one example of the entire sequence of a process of calculating the number of fluorescent molecules or the number of antibodies bonded to fluorescent molecules.
Figure 5:
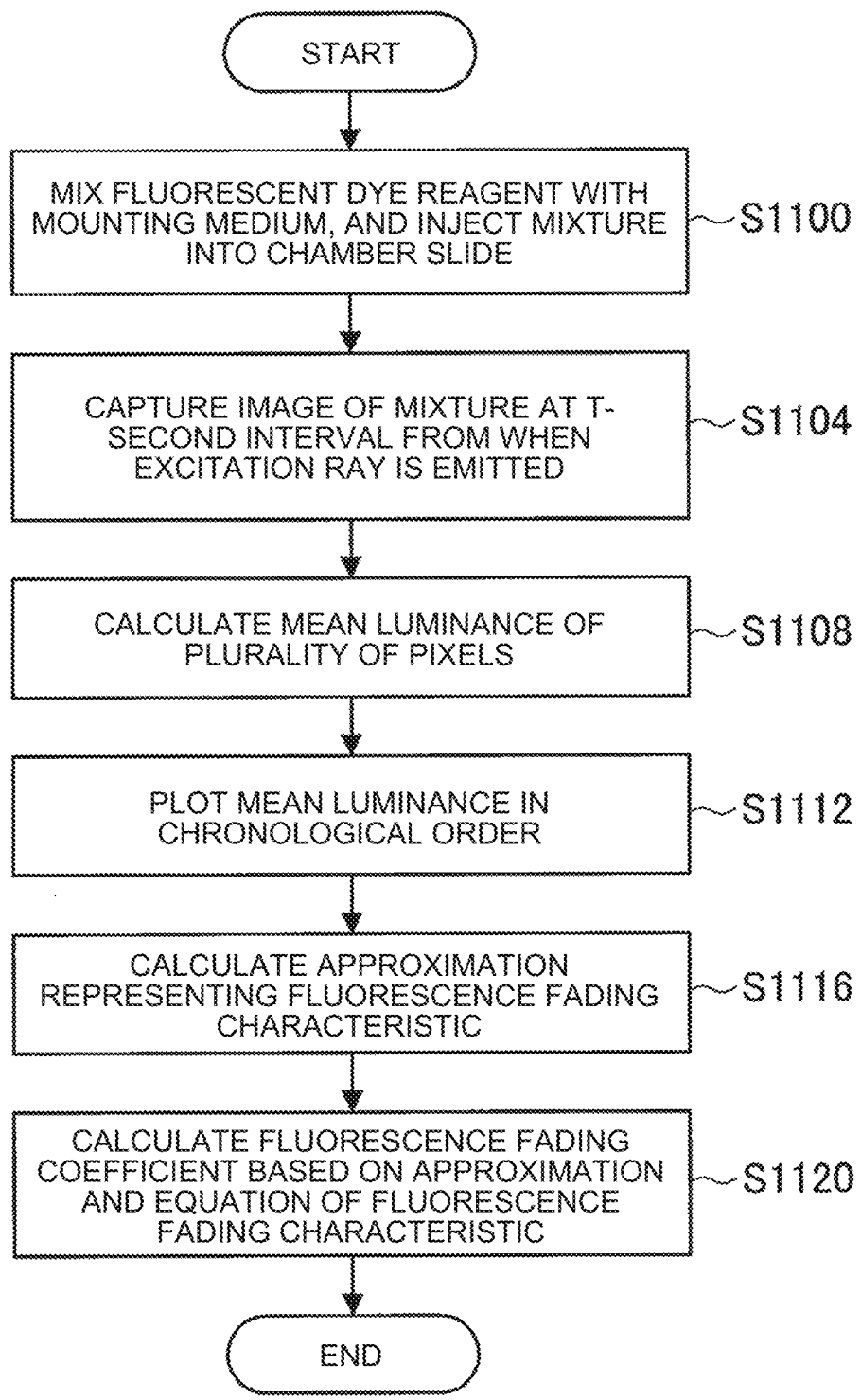
FIG. 5 is a flowchart illustrating an example of the sequence of a process of measuring a fluorescence fading coefficient.

As described earlier, in this embodiment, the measurement of the fluorescence fading coefficient is performed separately from the measurement of the number of fluorescent molecules or the like, and it is assumed that, when the measurement of the number of fluorescent molecules or the like is performed, the fluorescence fading coefficient of the fluorescent substance is acquired from the database 200 at Step S1012 in FIG. 2. This process of measuring the fluorescence fading coefficient will now be explained in detail with reference to FIG. 5. FIG. 5 illustrates a flowchart of the process of measuring the fluorescence fading coefficient by acquiring the captured image information of the fluorescent substance PE by mounting the imaging device (e.g., a CMOS) on an external port of the fluorescence microscope, and using the captured image information, as an example. The functional configuration for performing the measurement of the fluorescence fading coefficient is not limited to any particular configuration, but in the explanation hereunder, it is assumed that the calculating unit 132 of the information processing apparatus 100 performs the fluorescence fading coefficient measurement.

At Step S1100, a user mixes the fluorescent dye reagent 10 with the mounting medium, and injects the mixture into a chamber slide. The chamber slide is manufactured in such a manner that the gap between the slide glass and the cover glass remains constant, in advance (explained in this embodiment is an example in which used is a chamber slide having a gap of 10 [μm] between the slide glass and the cover glass), and, by using the chamber slide, the user can measure the fluorescence fading coefficient under the same condition every time the measurement is made. However, it is not necessarily needed to use a chamber slide, and the user may use a separate slide appropriately.

Furthermore, because the movement of the fluorescent substance is suppressed with the use of the mounting medium, it is possible to prevent entry of another fluorescent substance into the area where the image is captured, at the time at which the image is captured, or prevent a fluorescent substance having been present in the area where the image is captured from going out of the area where the image is captured. In this manner, more accurate calculation of the fluorescence fading coefficient can be achieved.

Figure 6:
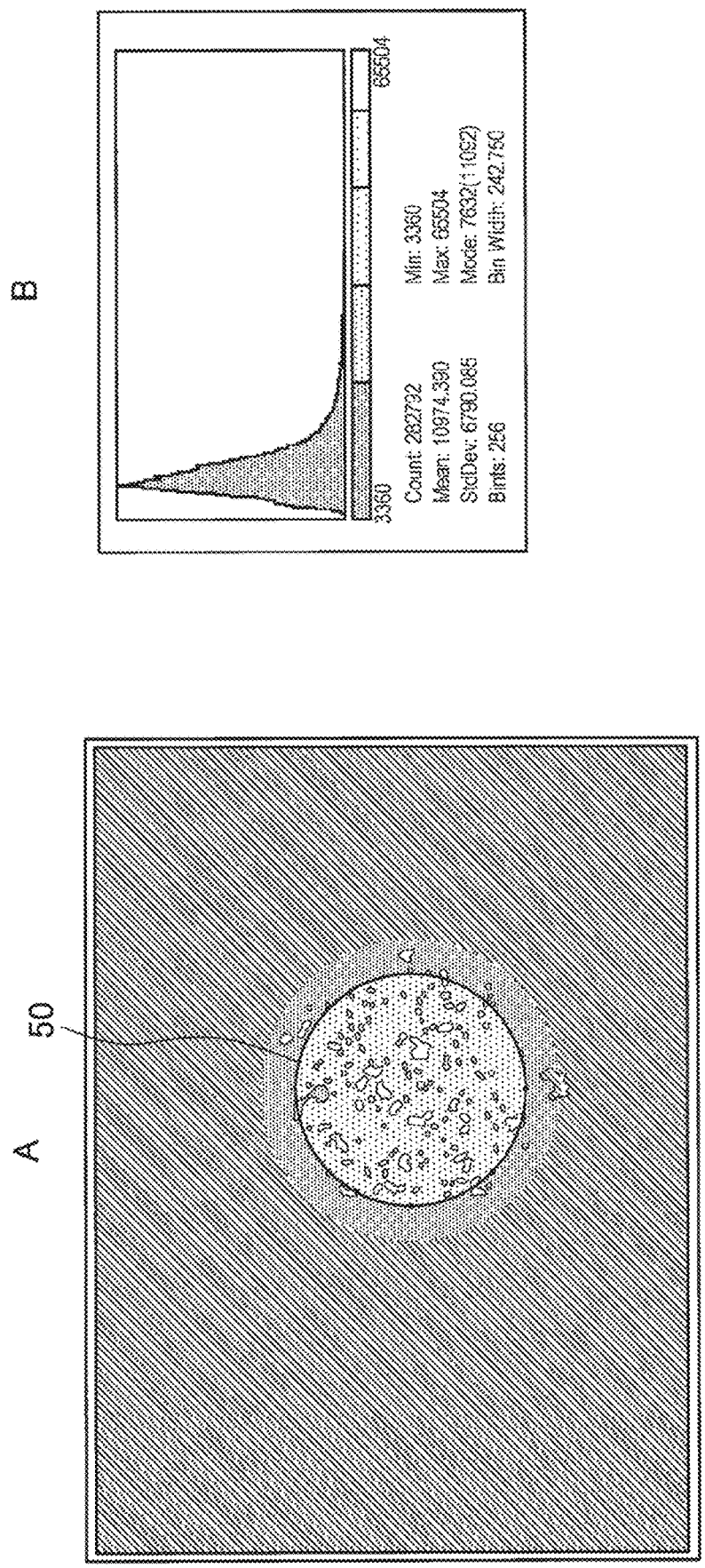
FIG. 6 is a schematic illustrating captured image information of a mixture of a fluorescent dye reagent 10 and a mounting medium.

At Step S1104, the image acquiring unit 112 captures an image of the mixture of the fluorescent dye reagent 10 and the mounting medium at a given interval (e.g., t-second interval) from when the excitation ray is emitted, using the imaging device (e.g., a CMOS) mounted on the external port of the fluorescence microscope. FIG. 6A illustrates captured image information immediately after the excitation ray is emitted, the captured image information being generated by the image capturing process at Step S1104. FIG. 6B illustrates the measurement results (histogram) achieved by a piece of image processing software that measures the luminance of a region 50 (a region where fluorescence is observed) including a plurality of pixels of the captured image information.

Figure 7:
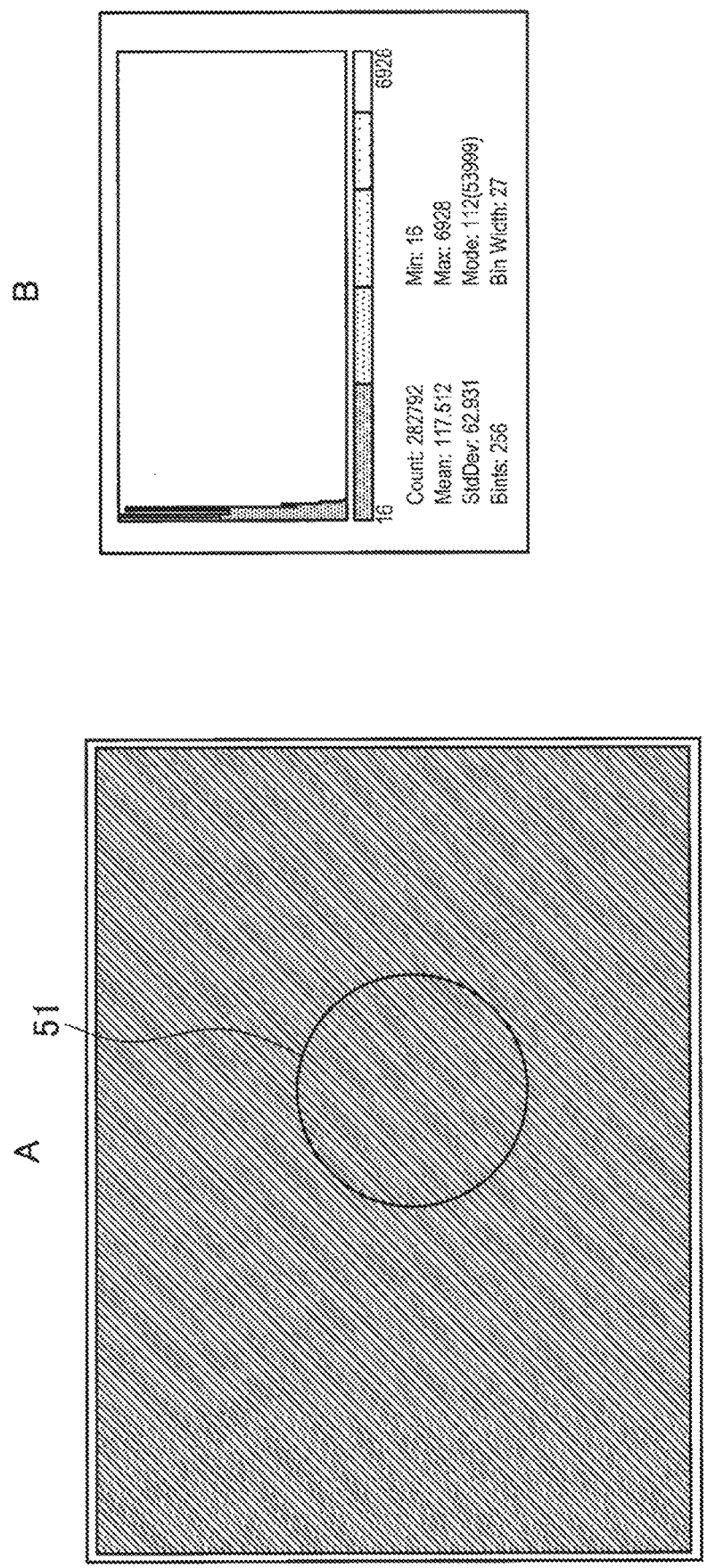
FIG. 7 is a schematic illustrating captured image information only of the mounting medium.

At Step S1108, the calculating unit 132 calculates the mean luminance of a plurality of pixels of the captured image information. At this time, because there are chances that the autofluorescence or the like unique to the chamber slide may be introduced, the user also prepares a chamber slide injected only with the mounting medium (without injecting the fluorescent dye reagent 10), and the image acquiring unit 112 is caused to capture the image of the chamber slide under the same conditions as those described above (it is suffice if an image of the chamber slide injected only with the mounting medium is captured only once, because the image is used for subtracting the background including the autofluorescence or the like). FIG. 7A illustrates captured image information of the chamber slide injected only with the mounting medium, immediately after the excitation ray is emitted. Furthermore, FIG. 7B illustrates the measurement results (histogram) achieved by a piece of image processing software that measures the luminance of a region 51 (assumingly a region substantially the same as the region 50) including a plurality of pixels of the captured image information. The calculating unit 132 then uses "Mean" in FIGS. 6B and 7B, as the mean luminance in the region 50 and the region 51, as indicated in Equation 20 below, for example, and the value (10856.878) resultant of subtracting the mean luminance of the region 51 (117.512) from the mean luminance of the region 50 (10974.390) is used as the mean luminance immediately after the excitation ray is emitted.

$$10974.390 - 117.512 = 10856.878 \tag{20}$$

Figure 8:
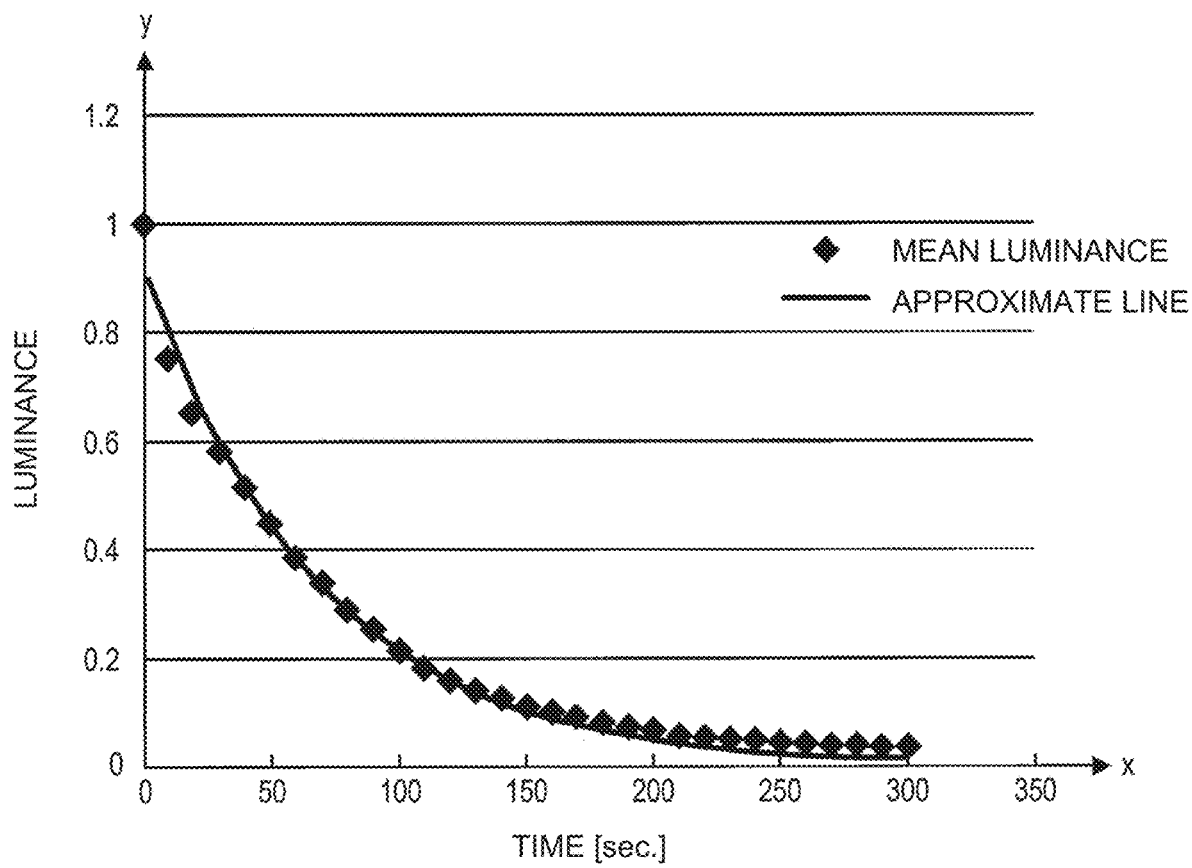
FIG. 8 is a schematic illustrating a result of plotting the mean luminance of a fluorescent substance in the chronological order.

At Step S1112, the calculating unit 132 then plots the mean luminance calculated in the manner described above in the chronological order. FIG. 8 illustrates the results of plotting the mean luminance measured at a 10 second-interval, until 300 seconds elapse from immediately after the excitation ray is emitted.

At Step S1116, the calculating unit 132 calculates an approximate line representing the mean luminance plotted in the chronological order. In the example of FIG. 8, the calculating unit 132 calculates the approximate line expressed as Equation 21 indicated below. The approximate line calculation method is not limited to any particular method, and the calculating unit 132 may use any method.

$$y(x) = 0.9128 \cdot e^{-0.0146x} \tag{21}$$

As described earlier, the fluorescence fading characteristic of the fluorescent substance is expressed as Equation 1 indicated above. Through a comparison of Equation 1 and Equation 21, it can be understood that "−(Abs photon)×φ" in Equation 1 is expressed as Equation 22, and therefore, the calculating unit 132 can calculate the fluorescence fading coefficient φ as indicated in Equation 23, by solving Equation 22 for the fluorescence fading coefficient φ. In other words, Equation 23 represents that the fluorescent substance having absorbed one photon, and having transited to the excited state does not go back to the ground state (the fluorescence goes through fluorescence fading) at a probability of 1.46 [%]. At this time, the calculating unit 132 calculates the fluorescence fading coefficient φ as indicated by Equation 24, by inputting the number of absorbed photons Abs photon calculated by the same operation as that indicated in Equation 5 to Equation 23 (Step S1120 in FIG. 5).

$$-(\text{Abs photon}) \times \phi = -0.0146 \tag{22}$$

$$\phi = \frac{0.0146}{\text{Abs photon}} \tag{23}$$

$$\phi = \frac{0.0146}{\text{Abs photon}} = \frac{0.0146}{1.07 \times 10^5 \,[\text{photon}/s/\text{molecule}]} \approx 1.36 \times 10^{-7} \tag{24}$$

3.7. Example of Sequence of Process of Measuring Quantum Yield

In this embodiment, it is assumed that the quantum yield is measured separately from the measurement of the number of fluorescent molecules or the like, in the same manner as for the fluorescence fading coefficient, and that, when the number of fluorescent molecules or the like is to be measured, the quantum yield of the fluorescent substance is acquired from the database 200 at Step S1012 in FIG. 2. (However, the embodiment is not limited thereto, and the measurement of the quantum yield and the measurement of the number of fluorescent molecules or the like may be performed at once).

Because the quantum yield of the fluorescent substance is greatly affected by the environment where the fluorescent substance is present (in particular, by the solvent), as generally published by a catalog specification, it is preferable to use an actual measurement calculated in the solvent environment that is the same as that for the fluorescent dye sample 30. For example, one example of results of comparisons between the actual measurement of a quantum yield calculated in a solvent environment that is the same as that for the fluorescent dye sample 30, and the quantum yield according to a catalog specification is illustrated in FIG. 9.

The functional configuration for performing the quantum yield calculation is not limited to any particular configuration, but in the explanation below, it is assumed that the calculating unit 132 of the information processing apparatus 100 performs the quantum yield calculation.

The quantum yield of the fluorescent substance is calculated by Equation 25 indicated below. Abs photon (absorbed photons) can be calculated by the same operation as that indicated by Equation 5.

$$\text{Quantum Yield} = \text{Number of Emitted Photons}/(\text{Abs photon}) \tag{25}$$

Figure 10:
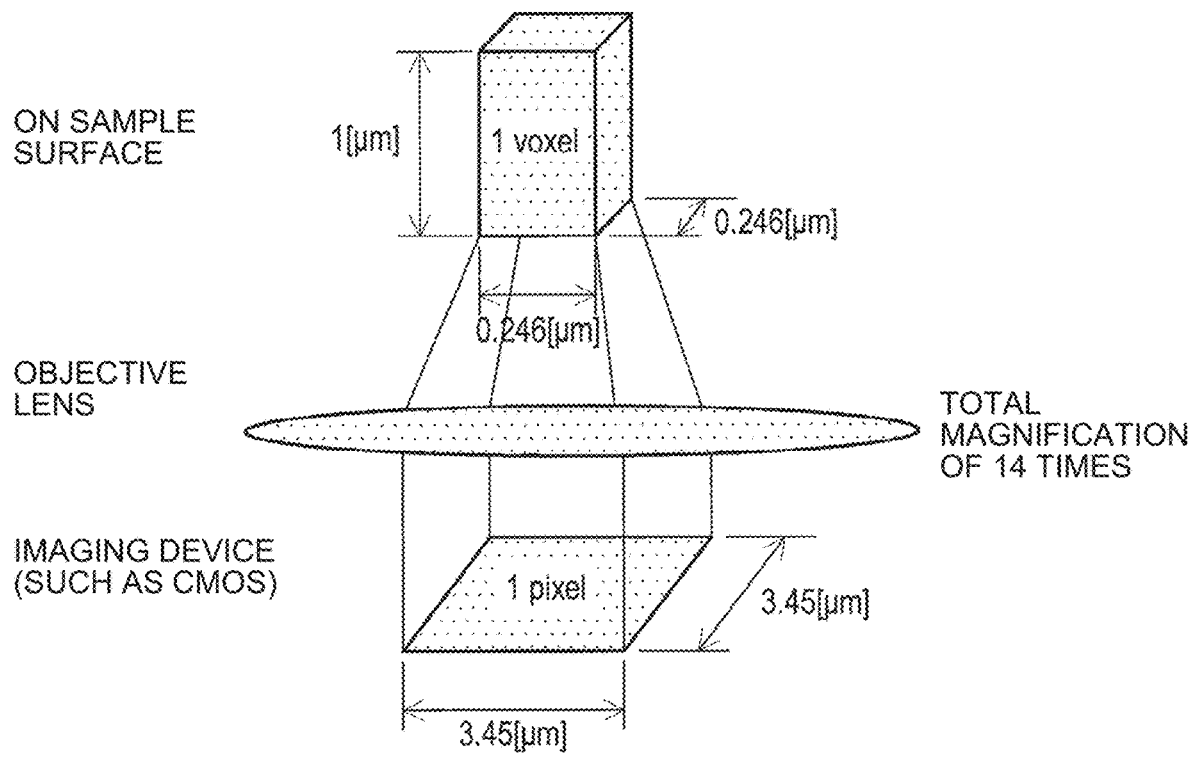
FIG. 10 is a schematic for explaining a method for calculating the number of emitted photons.

The method for calculating the number of emitted photons will now be explained. As illustrated in FIG. 10, a cuboid having a thickness of 1 [μm] and having a sample surface corresponding to one pixel of the imaging device (e.g., a CMOS) as the bottom surface is defined as one [voxel]. Assuming that one [pixel] of the imaging device has a size of 3.45 [μm]×3.45 [μm], and the total magnification of the objective lens is 14 [times], the size of the bottom surface on the sample surface corresponding to one [pixel] can be approximated as 0.246 [μm]×0.246 [μm]. Therefore, the volume of one [voxel] is expressed as 0.246 [μm]×0.246 [μm]×1 [μm].

Because the volume of one [voxel] can be calculated in the manner described above, the calculating unit 132 can calculate the number of fluorescent molecules that are present in one [voxel], using the actual measurement of the sample concentration. The sample concentration is calculated with the absorbance and the absorbance coefficient at the excitation wavelength, as indicated in Equation 26 below. It is assumed herein that the number of fluorescent molecules that are present in one [voxel] is N [molecules/voxel].

$$\text{Sample Concentration (Concentration of Fluorescent Substance)} = \frac{\text{Absorbance}}{\text{Absorbance Coefficient}} \tag{26}$$

The image acquiring unit 112 captures an image of the sample injected only with the mounting medium, in addition to that of the fluorescent substance, using an imaging device (e.g., a CMOS). The calculating unit 132 can cancel the background noise attributable to the measurement system by subtracting the measurement result for the sample injected only with the mounting medium, from the measurement result for the sample of the fluorescent substance.

The calculating unit 132 can calculate the mean luminance per one [pixel] of the captured image information, using some image processing software, and calculate the number of electrons per one [pixel] using Equation 27 indicated below. By using the mean luminance per one [pixel], it is possible to cancel out the unevenness of the dye solution, the measurement errors, and the like. It is assumed that the gradation of the captured image information is 16 [bits] (in other words, luminance takes a value between 0 and 65536). In Equation 27, the mean luminance of the captured image information of the sample of the fluorescent substance is denoted as "mean luminance 1", and the mean luminance of the captured image information of the sample injected only with the mounting medium is denoted as "mean luminance 2".

$$\text{Number of Electrons Per One [pixel]}[e-/s/\text{pixel}] = \frac{\text{Mean Luminance 1} - \text{Mean Luminance 2}}{65536[/\text{pixel}]} \times \text{Saturation} \tag{27}$$

$$\text{Charge of Imaging Device } [e-] \div \text{Exposure Time [s]}$$

The calculating unit 132 can calculate the number of electrons per one [pixel] by dividing the number of photons per one [pixel] by the quantum yield of the imaging device (e.g., a CMOS), as indicated in Equation 28 below.

$$\text{Number of Photons Per One [pixel]}[\text{photon}/s/\text{pixel}] = \frac{\text{Number of Electrons Per One [pixel]}}{\text{Quantum Yield of Imaging Device}} \tag{28}$$

Furthermore, the calculating unit 132 can calculate the number of emitted photons per one molecule per excitation power density of one [mW/cm$^2$] using Equation 29 indicated below. "1 [μm]" in Equation 29 represents the thickness of one [voxel], and "N [molecules/voxel]" represents the number of fluorescent molecules [molecules/voxel] that are present in one [voxel], calculated in the manner described above. The excitation power density is calculated in the same manner as in Equation 10 above (the unit is [mW/cm$^2$]).

$$\text{Number of Emitted Photons} \quad (29)$$

$$(\text{Per Molecule Per Excitation Power Density of One } [mW/cm^2]) =$$

$$\frac{\text{Number of Photons Per One [pixel]}}{\text{Excitation Power Density}[mW/cm2]} \times$$

$$\frac{1[\mu m]}{\text{Chamber Slide Thickness}} \times \frac{1}{N \text{ [molecules/voxel]}}$$

The luminance of the captured image information is a value related to the fluorescence detected through the objective lens of the fluorescence microscope, and the fluorescence emitted from the fluorescent substance is emitted in the full range. Therefore, the calculating unit 132 calculates a full-range conversion of the number of emitted photons as indicated in Equation 30 below, in the same manner as in Equation 15 indicated above.

$$\text{Number of Emitted Photons (Full − Range Conversion)} = \quad (30)$$

$$\left( \frac{\text{Number of Photons Per One [pixel]}}{\text{Excitation Power Density } [mW/cm2]} \times \frac{1\ [\mu m]}{\text{Chamber Slide Thickness}} \times \right.$$

$$\left. \frac{1}{N \text{ [molecules/voxel]}} \right) / \frac{1 - \cos(\arcsin(NA))}{2}$$

The calculating unit 132 can calculate the quantum yield of the fluorescent substance, by inputting Abs photon calculated with the same operation as Equation 5 above, and the number of emitted photons (full-range conversion) calculated with Equation 30 above, to Equation 25 described above.

4. Embodiment

An example of the sequence of a process performed by the information processing system according to the embodiment has been explained above. An embodiment in which the number of fluorescent molecules and the number of antibodies are calculated using the method described above will now be explained. More specifically, an example in which estrogen (ER) in breast cancer tissues are dyed with fluorescent substance AF647 (AlexaFluor 647) will now be explained.

The calculating unit 132 calculates the absorption cross section by inputting the molar absorbance coefficient & of ER 239000 [L/mol/cm] to Equation 11 indicated above, instead of the molar absorbance coefficient & of PE 1960000 [L/mol/cm] (as described earlier, the calculated absorption cross section is managed in the database 200).

$$\text{Absorption Cross Section} = \quad (11)$$

$$\frac{239000[\text{L/mol/cm}] \times 1000[\text{cm}^3] \times 2.3}{6.02 \times 10^{23}[\text{molecules}]} \approx 9.13 \times 10^{-16} [\text{cm2/molecule}]$$

The calculating unit 132 also calculates the energy of one [photon] using Equation 7 indicated above.

$$\text{Energy of One [photon]} = \frac{h \times c}{\lambda} \approx 3.16 \times 10^{-19} [\text{J}] \quad (7)$$

h: Planck Constant (6.62×10$^{-34}$ [Js])
c: Light Speed in Vacuum (3.00×10$^8$ [m/s])
λ: Wavelength of Electromagnetic Wave in Vacuum (In This Embodiment, 628×10$^{-9}$ [m])

The calculating unit 132 also calculates the excitation photon density using Equation 6 indicated above. For the excitation power density, a value actually measured in the embodiment (1.14 [W/cm$^2$]) is used (as described earlier, the measured excitation power density is managed in the database 200).

$$\text{Excited Photon Density} = \frac{\text{Excitation Power Density}}{\text{Energy of One [photon]}} \approx \quad (6)$$

$$\frac{1.14[\text{W/cm}^2]}{3.16 \times 10^{-19}[\text{J}]} \approx 3.61 \times 10^{-18} [\text{photon/s/cm}^2]$$

The calculating unit 132 also calculates the number of absorbed photons (Abs photon), using Equation 5 indicated above.

(Abs photon)=Excited Photon Density×Absorption Cross Section ≈3.61×10$^{-18}$ [photon/s/cm$^2$]× 9.13×10$^{-16}$ [cm2/molecule]≈3.30×10$^3$ [photon/s/molecule]   (5)

It is now assumed that the fluorescence fading coefficient is calculated as φ=1.06×10$^{-6}$, with the number of absorbed photons (Abs photon). The calculating unit 132 then calculates the initial value F$_0$ using Equation 3 indicated above. It is assumed herein that the exposure time is t=0.125 [seconds].

$$F_0 = \text{Actual Measurement of Fluorescence Intensity}/ \quad (3)$$

$$\left\{ \frac{1 - \text{Exp}(-(\text{Abs photon}) \times \phi \times t)}{(\text{Abs photon}) \times \phi} \right\}$$

$$\approx \text{Actual Measurement of Fluorescence Intensity}/$$

$$\left\{ \frac{1 - \text{Exp}(-(3.30 \times 10^3 \times 1.06 \times 10^{-6} \times 0.125))}{3.30 \times 10^3 \times 1.06 \times 10^{-6}} \right\}$$

$$\approx \text{Actual Measurement of Fluorescence Intensity}/$$

$$0.125 = \text{Actual Measurement of Fluorescence Intensity} \times 8.00$$

The calculating unit 132 then calculates the fluorescence intensity after the fluorescence fading correcting process, using Equation 4 indicated above.

Fluorescence Intensity After Fluorescence Fading Correction=$F_0$×t=Actual Measurement of Fluorescence Intensity×8.00×0.125=Actual Measurement of Fluorescence Intensity×1.00

Figure 11:
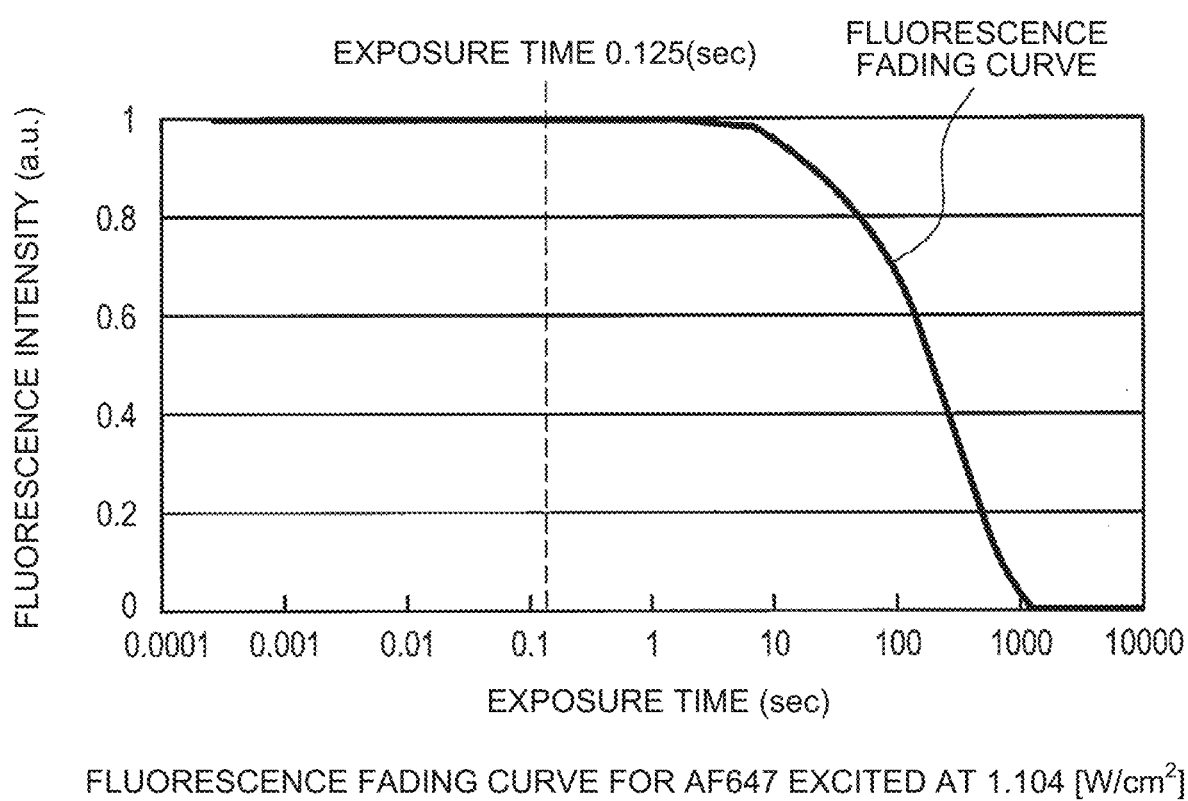
FIG. 11 is a schematic illustrating a fluorescence fading curve of a fluorescent substance AF647 excited at an excitation power density of 1.104 [W/cm$^2$].

As indicated in Equation 4, the fluorescence intensity after the fluorescence fading correcting process and the actual measurement of the fluorescence intensity take the same value. This means that, when the fluorescent substance AF647 is excited at an excitation power density of 1.104 [W/cm$^2$], the fluorescent substance does not go through fluorescence fading in the exposure time 0.125 [seconds] almost at all, as illustrated in FIG. 11 (FIG. 11 is a schematic illustrating a fluorescence fading curve of the fluorescent substance AF647 when the fluorescent substance AF647 is excited at the excitation power density of 1.104 [W/cm$^2$]).

The calculating unit 132 converts the luminance at each pixel into the number of photons, using the values calculated in the process described above, and converts the number of photons into the number of fluorescent molecules and the number of antibodies. More specifically, the calculating unit 132 calculates the number of electrons at a pixel A using Equation 12 indicated above, and calculates the number of photons at the pixel A using Equation 13 indicated above. Because, in this embodiment, a gain adjustment has been performed when an image is captured, a division by 17.8 [times] is performed in Equation 12 indicated below so that the adjusted amount is cancelled out.

$$\text{Number of Electrons at Pixel } A[e-/s/\text{pixel}] = \tag{12}$$
$$\frac{\text{Luminance 1} - \text{Luminance 2}}{65536[/\text{pixel}]} \times \text{Saturation}$$
$$\text{Charge of Imaging Device}[e-] \times \frac{1}{\text{Exposure Time}[s]} =$$
$$\frac{N/17.8[\text{Times}]}{65536[/\text{pixel}]} \times 10482[e-] \times \frac{1}{0.125[s]}$$

$$\text{Number of Photons at Pixel } A[\text{photon}/s/\text{pixel}] = \tag{13}$$
$$\frac{\text{Number of Electrons at Pixel } A}{\text{Quantum Yield of Imaging Device}} =$$
$$\frac{N/17.8[\text{Times}]}{65536[/\text{pixel}]} \times 10482[e-] \times \frac{1}{0.125[s]} \times \frac{1}{0.668}$$

The calculating unit 132 then converts the number of photons to the number of fluorescent molecules, using Equation 16 indicated above.

$$\text{Number of Fluorescent Molecule at Pixel } A = \tag{16}$$
$$\frac{\frac{\text{Number of Photons Detected at Pixel } A}{(\text{Full} - \text{Range Conversion})}}{\text{Number of Emitted Photons Per One Molecule}} \approx$$
$$\frac{N/17.8[\text{Times}]}{65536[/\text{pixel}]} \times 10482[e-] \times \frac{1}{0.125[s]} \times \frac{1}{0.668} \times \frac{1}{9.311376} \approx$$
$$N/0.0116[\text{molecule/pixel}]$$

Above Equation 16 indicates that a value resultant of multiplying 0.0116 to the luminance at each pixel of the captured image information is equal to the number of fluorescent molecules. In other words, by converting the luminance at each pixel to the number of fluorescent molecules, the information processing apparatus 100 can compress the information (at a compression ratio of 1.16 [%]).

FIG. 12A illustrates that the captured image information applied with the fluorescence fading correcting process has a gradation of 16 [bits], and FIG. 12B illustrates the captured image information. FIG. 13A illustrates that the image information generated by converting the luminance of each pixel into the number of fluorescent molecules has a gradation of 10 [bits], and FIG. 13B illustrates the image information. As it may be understood by comparing FIGS. 12B and 13B, after the information is compressed by converting the luminance into the number of fluorescent molecules, the user can recognize the number of fluorescent molecules appropriately (or a user can compare the numbers of fluorescent molecules among different fluorescent molecules appropriately) even with a reduced number of gradations.

The calculating unit 132 also converts the number of fluorescent molecules into the number of antibodies, using Equation 18 indicated above.

$$\text{Number of Antibodies at Pixel } A = \tag{18}$$
$$\frac{\text{Number of Fluorescent Molecule at Pixel } A}{\text{Fluorescent Labeling Rate}} \approx$$
$$\frac{N/17.8[\text{Times}]}{65536[/\text{pixel}]} \times 10482[e-] \times \frac{1}{0.125[s]} \times \frac{1}{0.668} \times \frac{1}{9.311376} \times \frac{1}{3.5} \approx$$
$$N \times 0.00330[\text{protein/pixel}]$$

Above Equation 18 indicates that a value resultant of multiplying 0.00330 to the luminance at each pixel of the captured image information is equal to the number of antibodies. In other words, by converting the luminance at each pixel into the number of antibodies, the information processing apparatus 100 can compress the information (at a compression ratio of 0.330 [%]). FIG. 14A illustrates that the image information generated by converting the luminance of each pixel into the number of antibodies has a gradation of 8 [bits], and FIG. 14B illustrates the image information. As it may be understood by comparing FIGS. 12B and 14B, after the information is compressed by converting the luminance into the number of antibodies, a user can recognize the number of antibodies appropriately (or, a user can compare the numbers of antibodies among different antibodies, appropriately), even with a reduced number of gradations.

FIG. 15 illustrates actual measurements of the number of photons per one molecule, the image compression ratio reflected with the number of fluorescent molecules, the fluorescent labeling ratio, the image compression ratio reflected with the number of antibodies, having been measured for each of the fluorescent substances (the values pertinent to "AF647" in FIG. 15 are calculated under different conditions as those used in the embodiment described above).

5. Correction Related to Fluorescence Saturation

Explained in the description above is an embodiment in which the number of fluorescent molecules and the number of antibodies are calculated. An example in which a correction related to a fluorescence saturation is performed will now be explained.

"Fluorescence saturation" is a phenomenon in which fluorescent molecules to be excited fall short as a result of the fluorescent molecules being irradiated with the excitation ray and transiting to the excited state. In other words, after the fluorescence saturation has been reached, how much ever the fluorescent molecules are irradiated with the excitation ray, no more fluorescent molecules go into the excitation state, and emits no fluorescence.

Figure 16:
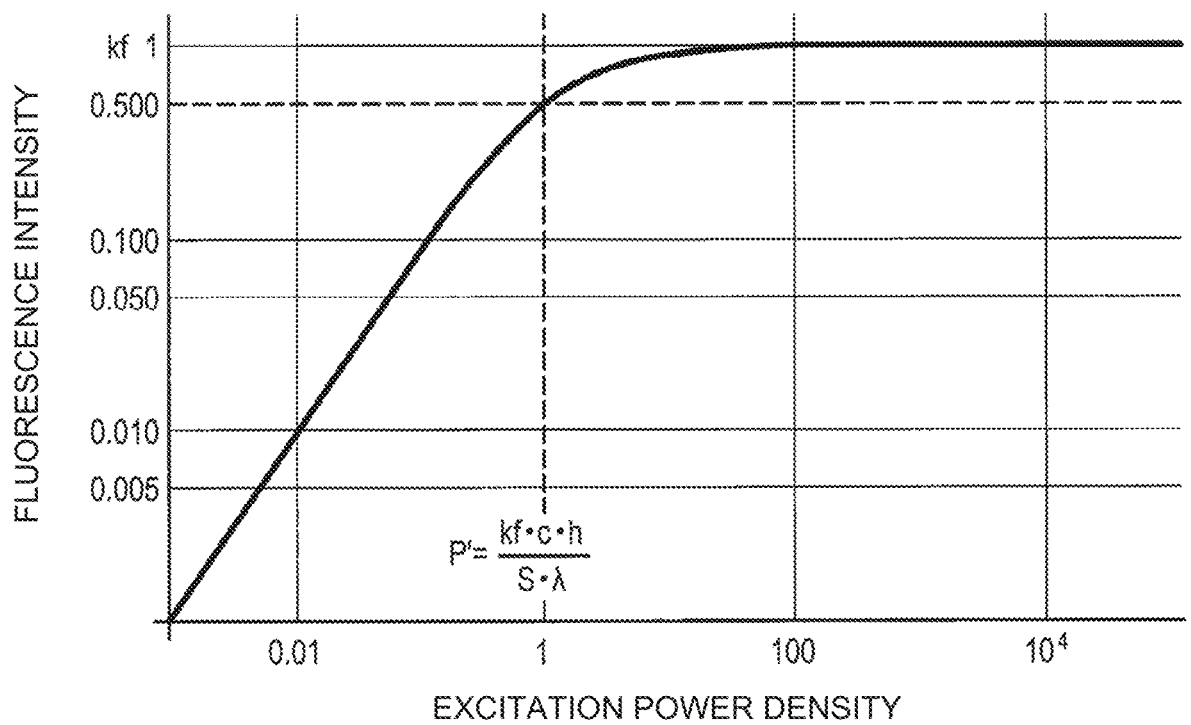
FIG. 16 is a log-log graph illustrating a relation between an excitation power density at which an excitation ray is emitted, and a fluorescence intensity of the fluorescence caused by the emission of the excitation ray.

FIG. 16 is a log-log graph illustrating a relation between the excitation power density at which an excitation ray is emitted, and a fluorescence intensity of the fluorescence caused by the emission of the excitation ray. As illustrated in FIG. 16, the fluorescence intensity increases in proportion to the excitation power density, but the amount of the increase gradually becomes smaller as the excitation power density is increased. Once the excitation power density exceeds a certain level and reaches the fluorescence saturation, the fluorescence intensity does not become any higher than kf (hereinafter, referred to as a "saturation fluorescence intensity") how much ever the excitation power density is increased.

To address this issue, in this embodiment, it is possible to perform a correction taking the effect of the fluorescence saturation into consideration. More specifically, the actual measurement of the saturation fluorescence intensity kf is collected in advance, and a correction may be performed by multiplying a correction equation related to fluorescence saturation indicated below as Equation 31 to "the number of emitted photons per one molecule" in Equation 16 indicated above (the equation for calculating the number of fluorescent molecules at the pixel A). In other words, the correcting unit 131 may perform not only the correction using the fluorescence fading coefficient, but also a correction related to the fluorescence saturation, to the luminance of the captured image information (the calculating unit 132 then calculates the number of fluorescent molecules and the number of antibodies using the corrected luminance of the captured image information).

$$P_{fl} = \frac{kf \cdot P \cdot S \cdot \lambda}{kf \cdot h \cdot c + P \cdot S \cdot \lambda} = \frac{kf \cdot P}{P + \frac{kf \cdot c \cdot h}{S \cdot \lambda}} \quad (31)$$

$P_{fl}$: Fluorescence Intensity
kf: Saturation Fluorescence Intensity
h: Planck Constant ($6.62607 \times 10^{-34}$ [S])
c: Light Speed in Vacuum ($2.99792458 \times 10^{8}$ [m/s])
P: Excitation Power Density
S: Scattering Cross Section (=Absorption Cross Section× Quantum Yield)
λ: Wavelength of Electromagnetic Wave in Vacuum (In This Embodiment, $543 \times 10^{-9}$ [m] As One Example)

At this time, due to the characteristics of Equation 31 mentioned above, an excitation power density P' where the fluorescence intensity becomes a half the saturation fluorescence intensity kf is indicated by Equation 32 below (see FIG. 16). In other words, by solving Equation 31 with the substitution $P_{fl}$=kf/2, Equation 32 is derived.

$$P' = \frac{kf \cdot c \cdot h}{S \cdot \lambda} \quad (32)$$

Figure 17:
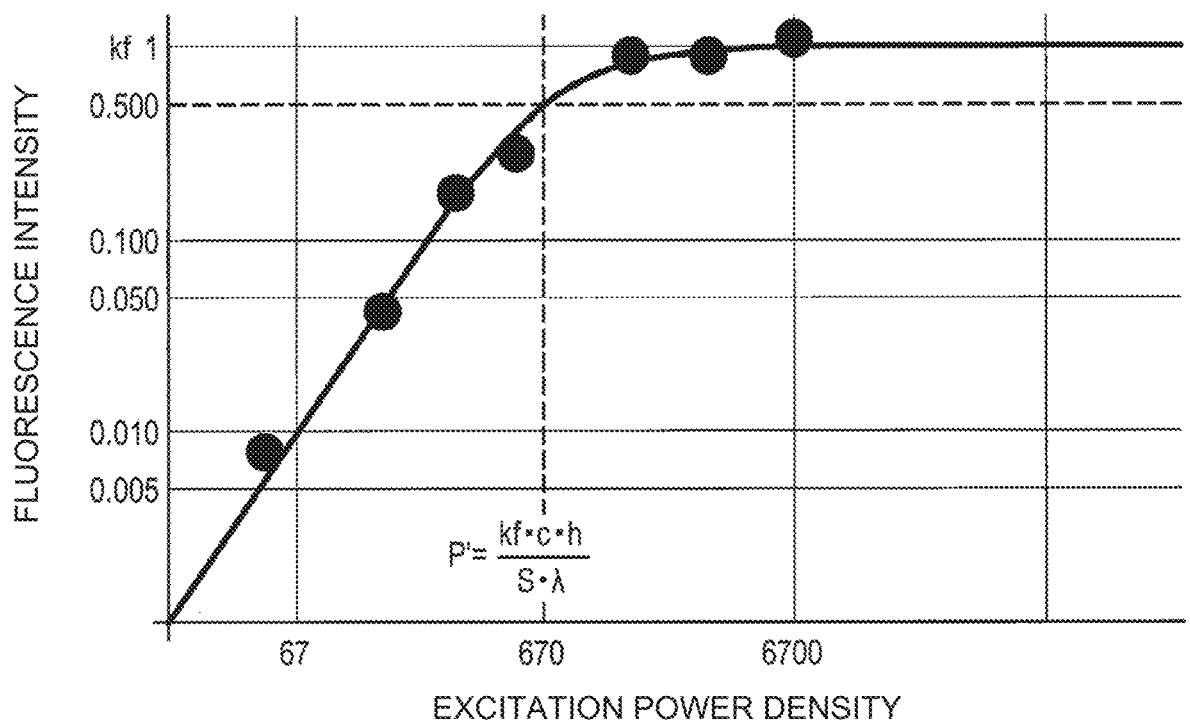
FIG. 17 is a schematic for explaining a method for calculating a saturation fluorescence intensity.

P': Excitation Power Density Where Fluorescence Intensity Becomes Half Saturation Fluorescence Intensity kf Based on the above, the saturation fluorescence intensity kf is actually measured. More specifically, a process of irradiating the fluorescent dye sample 30 with the excitation ray, and measuring the fluorescence intensity of the fluorescence caused by the emission of the excitation ray is performed for a plurality of excitation power densities. The saturation fluorescence intensity kf is then calculated by plotting the measurement results carried out for the respective excitation power densities, and fitting the plot to Equation 31, as illustrated in FIG. 17.

A specific example of the calculation of the saturation fluorescence intensity kf will now be explained. For example, it is assumed that, when PE that is a type of fluorescence component is used, a relation P'≈$6.7 \times 10^{4}$ [W/cm$^2$] is acquired for Equation 32, through the fitting using Equation 31. At this time, it is assumed that a relation c·h/λ=$3.66 \times 10^{-19}$ [J] is established, as indicated in Equation 7. For the scattering cross section S(=absorption cross section×quantum yield), because a relation absorption cross section≈$7.49 \times 10^{-15}$ [cm$^2$/molecule] is established, as indicated in Equation 11, when the actual measurement of 0.483 (or the catalog specification of 0.840) of the quantum yield of PE, as illustrated in FIG. 9, is used, a relation of the scattering cross section S=3.62 [cm$^2$/molecule] (or 6.29 [cm$^2$/molecule]) is established.

By solving Equation 32 based on the above, the saturation fluorescence intensity kf=$6.7 \times 10^{4}$ [W/cm$^2$]×3.62 [cm$^2$/molecule] (or 6.29 [cm$^2$/molecule])/($3.66 \times 10^{-19}$ [J])≈$0.66 \times 10^{24}$ [Photons/s/molecule] (or $1.2 \times 10^{24}$ [Photons/s/molecule]) is established.

The implementor performs the correction related to the fluorescence saturation by substituting the actual measurement of the saturation fluorescence intensity kf acquired in the manner described above, into correction Equation 31 related to the fluorescence saturation, and by multiplying the calculation result to "the number of emitted photons per one molecule" in Equation 16. In this manner, it is possible to calculate the number of fluorescent molecules or the number of antibodies highly accurately regardless of the excitation power density, by taking the effect of the fluorescence saturation into consideration.

The timing at which the saturation fluorescence intensity kf is actually measured is not limited to any particular timing. For example, the saturation fluorescence intensity kf may be actually measured prior to the experiments for measuring the number of fluorescent molecules and the number of antibodies, or the actual measurement may be collected during measurement experiments.

<6. Exemplary Hardware Configuration>

One embodiment of the present disclosure has been explained above. An exemplary hardware configuration of the information processing apparatus 100 will now be explained. The various processes explained above are implemented by cooperation of software and hardware to be explained below.

Figure 18:
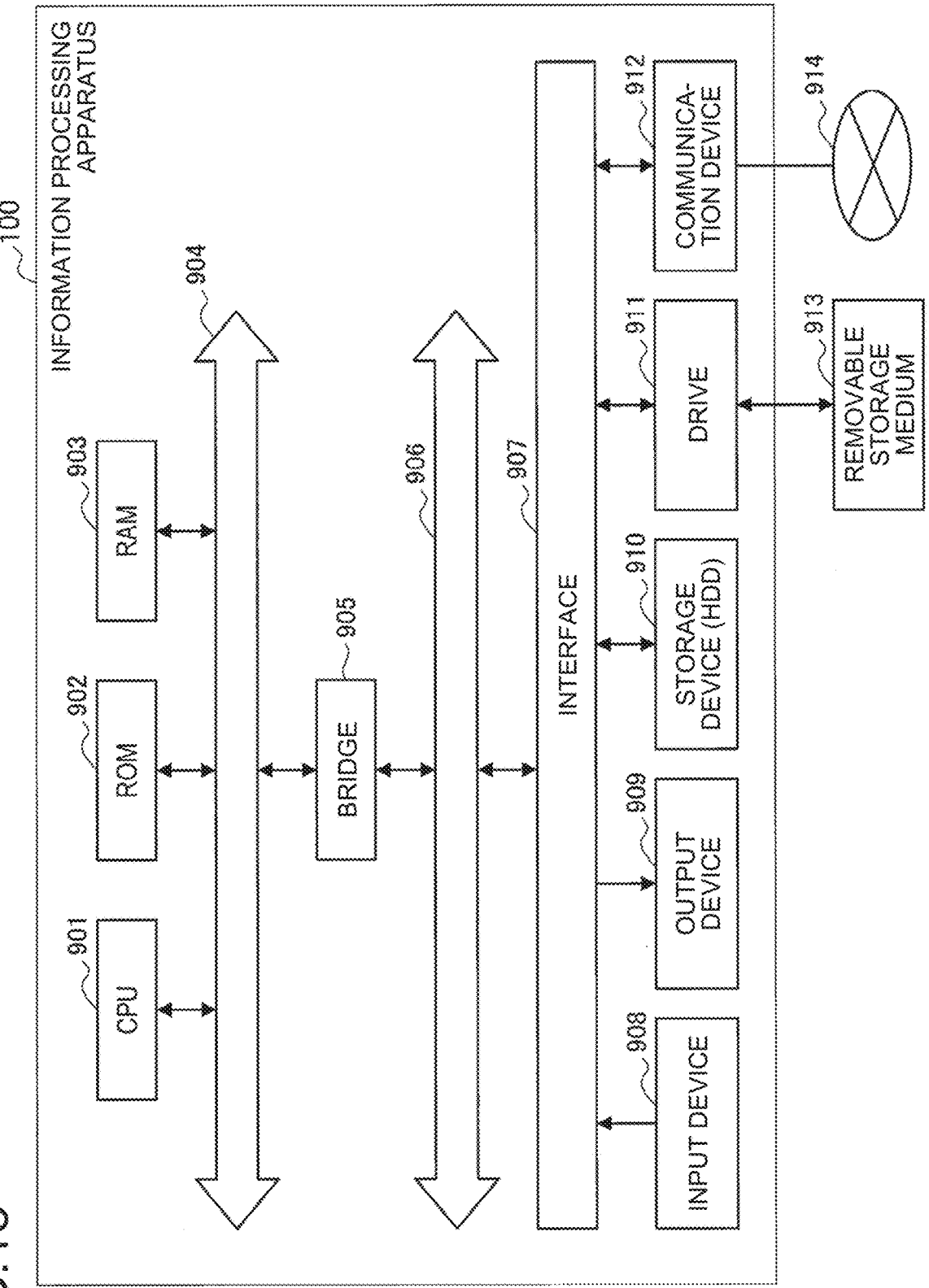
FIG. 18 is a block diagram illustrating an exemplary hardware configuration of an information processing apparatus 100.

FIG. 18 is a block diagram illustrating an exemplary hardware configuration of the information processing apparatus 100. The information processing apparatus 100 includes a central processing unit (CPU) 901, a read-only memory (ROM) 902, a random access memory (RAM) 903, a host bus 904, a bridge 905, an external bus 906, an interface 907, an input device 908, an output device 909, a storage device (HDD) 910, a drive 911, and a communication device 912.

The CPU 901 functions as an operation processor device and a control device, and controls the overall operation of the information processing apparatus 100, in accordance with various computer programs. The CPU 901 may also be a microprocessor. The ROM 902 stores therein computer programs, operation parameters, and the like used by the CPU 901. The RAM 903 temporarily stores therein computer programs used in executions of the CPU 901, and parameters or the like that changes as appropriate, during the execution. These elements are connected to one another via the host bus 904 configured as a CPU bus, for example. The functions of the processing unit 130 and the control unit 150 are implemented by the cooperation of the CPU 901, the ROM 902, and the RAM 903.

The host bus 904 is connected to the external bus 906 such as a peripheral component interconnect/interface (PCI) bus, via the bridge 905. The host bus 904, the bridge 905, and the external bus 906 do not necessarily need to be configured separately, and the functions of these buses may be implemented in one bus.

The input device 908 functions as a device such as a mouse, a keyboard, a touch panel, a button, a microphone, a switch, a lever, or various sensors (including the imaging device) for allowing a user to enter information, and is configured as an input control circuit or the like that generates an input signal based on a user input, and that outputs the signal to the CPU 901. The input device 908 implements a part of the function of the acquiring unit 110, and the function of the operation unit 160.

The output device 909 includes a display device such as a cathode ray tube (CRT) display device, a liquid crystal display (LCD) device, an organic light-emitting diode (OLED) device, and a lamp. The output device 909 includes an audio output device such as a speaker or a headset. The output device 909 displays various types of information such as video data as an image or a text. The audio output device converts audio data or the like into audio, and outputs the audio. The output device 909 implements the function of the display unit 140.

The storage device 910 is a device for storing therein data. The storage device 910 may include a recording device for recording data in a storage medium, a reader device for reading data from the storage medium, and a deleting device for deleting data recorded in the storage device. The storage device 910 is configured as a hard disk drive (HDD), for example. The storage device 910 drives the hard disk, and stores therein computer programs executed by the CPU 901, and various types of data. The storage device 910 implements the function of the storage unit 120.

The drive 911 is a reader/writer for a storage medium, and provided internally or externally to the information processing apparatus 100. The drive 911 reads information recorded in a removable storage medium 913, such as a magnetic disk, an optical disk, an opto-magnetic disk, or a semiconductor memory, mounted thereon, and outputs the information to the RAM 903. The drive 911 is also capable of writing information to the removable storage medium 913.

The communication device 912 is a communication interface configured as a communication device connected to a communication network 914, for example. The communication device 912 implements the function of a part of the acquiring unit 110.

The hardware configuration of the information processing apparatus 100 is not limited to the configuration illustrated in FIG. 18. For example, it is possible for the information processing apparatus 100 not to be provided with the communication device 912 when a communication is to be carried out via an external communication device connected thereto. The communication device 912 may also be configured to communicate using a plurality of communication protocols. Furthermore, for example, a part or the whole of the configuration illustrated in FIG. 18 may be implemented in one, or two or more integrated circuits (ICs).

7. Remarks

In the description above, an exemplary hardware configuration of the information processing apparatus 100 has been explained. A method for deriving the ratio of a detectable area through an objective lens, with respect to the full range about the radiant point 42 of the fluorescence (Equation 14 indicated above) will now be explained.

When the range 40 where the fluorescence is detectable through the objective lens is a conical part of a sphere that has the radiant point 42 of the fluorescence as its center, as illustrated in FIG. 19A, the ratio of the range 40 with respect to the full range about the radiant point 42 of the fluorescence can be said to be a ratio of the surface area surrounded by a circle 41 in the conical part with respect to the surface area of the sphere that has the radiant point 42 of the fluorescence as its center. FIG. 19B is a cross-sectional view of a sphere when the cone is viewed laterally. Because the radius of the circle having the band-shaped section 43 illustrated in FIG. 19B as a circumference is expressed as $r \times \sin\theta$, the circumferential length of the band-shaped section 43 is expressed as $2\pi r \times \sin\theta$. Furthermore, the width dx of the band-shaped section 43 is expressed as $r \times d\theta$. Therefore, the area of the band-shaped section 43 is expressed as Equation 33 indicated below.

$$\text{Area of Band-Shaped Section } 43 = 2\pi r \times \sin\theta \times r \times d\theta = 2\pi r^2 \times \sin\theta \times d\theta \quad (33)$$

The surface area surrounded by the circle 41 of the conical part on the sphere is acquired by taking an integration of Equation 33, as expressed in Equation 34 indicated below.

$$\text{Surface Area Surrounded By Circle 41 on Sphere} = \int_0^\theta 2\pi r^2 \times \sin\theta' \times d\theta' = 2\pi r^2 (1 - \cos\theta) \quad (34)$$

Because the surface area of the sphere that has the radiant point 42 of the fluorescence as its center is $4\pi r^2$, the ratio of the surface area surrounded by the circle 41 on the sphere with respect to the surface area of the sphere that has the radiant point 42 of the fluorescence as its center is expressed as Equation 35 indicated below.

$$\text{Ratio of Surface Area Surrounded By Circle 41 On Sphere with Respect to Sphere} = \frac{2\pi r^2 (1 - \cos\theta)}{4\pi r^2} = \frac{1 - \cos\theta}{2} \quad (35)$$

The relation between the numerical aperture NA of the objective lens and a half the apex angle $\theta$ is expressed as Equation 36 indicated below. In Equation 36, because n=1 unless an immersion lens is used as the objective lens (that is, because the refractive index of the air=1), by finally modifying Equation 35 is with the result of Equation 36, Equation 14 indicated above is derived.

$$NA = n \times \sin\theta \quad (36)$$

n: Refractive Index of Medium

8. Summary

As explained above, the information processing apparatus 100 according to the present disclosure acquires captured image information of the sample 20 dyed with the fluorescent dye reagent 10, the reagent information, and the like, and corrects the luminance of the captured image information using a fluorescence fading coefficient included in the reagent information. The information processing apparatus 100 can then calculate information corresponding to the fluorescent molecules (e.g., the number of fluorescent molecules or the number of antibodies bonded to fluorescent molecules) in the captured image information using the corrected luminance, and output image information reflected with the information.

In other words, the information processing apparatus 100 can output image information based on the number of fluorescent molecules, for example, instead of the luminance of the captured image information. In this manner, the information processing apparatus 100 can implement a quantitative evaluation, without depending on the measurement condition or the characteristics of the fluorescent substance. In particular, the information processing apparatus 100 can achieve a comparison in the number of fluorescent molecules, among a plurality of fluorescent substances or the like, more appropriately.

A preferred embodiment according to the present disclosure has been explained above with reference to the appended drawings, but the technical scope of the present disclosure is not limited to this example. It is clear that those having the ordinary knowledge in the technical field of the present disclosure can arrive at various changed examples or modified examples within the scope of the technical idea defined in the appended claims, and it is acknowledged that such changed or modified examples naturally fall within the technical scope of the present disclosure.

The effects described herein are merely explanatory and exemplary, and are not limiting. In other words, the technology according to the present disclosure can achieve other effects that are clear to those skilled in the art, together with or instead of the effects described above.

The following configurations also fall within the technical scope of the present disclosure.

(1)
An information processing apparatus comprising:
  an image acquiring unit that acquires captured image information of a sample dyed with a fluorescent dye reagent;
  an information acquiring unit that acquires information related to the fluorescent dye reagent;
  a correcting unit that corrects luminance of the captured image information using a fluorescence fading coefficient that represents rapidness at which a fluorescence intensity of the fluorescent dye reagent drops, the fluorescence fading coefficient being included in the information related to the fluorescent dye reagent; and
  a calculating unit that calculates information corresponding to fluorescent molecules in the captured image information, using the corrected luminance.

(2)
The information processing apparatus according to (1), wherein the information corresponding to fluorescent molecules includes at least one of number of fluorescent molecules and number of antibodies bonded to the fluorescent molecules.

(3)
The information processing apparatus according to (2), wherein the fluorescence intensity or the luminance is a continuous value, and the number of fluorescent molecules or the number of antibodies is a discrete value.

(4)
The information processing apparatus according to (2) or (3), wherein the information related to the fluorescent dye reagent at least includes a quantum yield, and an absorption cross section or a molar absorbance coefficient of the fluorescent dye reagent.

(5)
The information processing apparatus according to (4), wherein the information acquiring unit acquires the information related to the fluorescent dye reagent based on reagent identification information capable of identifying the fluorescent dye reagent.

(6)
The information processing apparatus according to (5), wherein the reagent identification information is also capable of identifying a production lot of the fluorescent dye reagent.

(7)
The information processing apparatus according to any one of (1) to (6), further comprising a display unit that displays image information generated based on the information corresponding to fluorescent molecules.

(8)
The information processing apparatus according to any one of (1) to (7), wherein the fluorescence fading coefficient is defined by number of photons absorbed by a fluorescent substance in the fluorescent dye reagent or a probability at which fluorescence of the fluorescent substance fades per excitation power density.

(9)
The information processing apparatus according to any one of (1) to (8), wherein the fluorescence fading coefficient is calculated separately using a sample that is different from that used in calculating the information corresponding to fluorescent molecules.

(10)
The information processing apparatus according to any one of (1) to (9), wherein
  the correcting unit also performs a correction related to fluorescence saturation to the luminance of the captured image information, and
  the calculating unit calculates the information corresponding to fluorescent molecules in the captured image information using the corrected luminance.

(11)
An information processing method executed by a computer, the information processing method comprising:
  acquiring captured image information of a sample dyed with a fluorescent dye reagent;
  acquiring information related to the fluorescent dye reagent;
  correcting luminance of the captured image information using a fluorescence fading coefficient that represents rapidness at which a fluorescence intensity of the fluorescent dye reagent drops, the fluorescence fading coefficient being included in the information related to the fluorescent dye reagent; and
  calculating information corresponding to fluorescent molecules in the captured image information, using the corrected luminance.

(12)
A computer program causing a computer to execute:
  acquiring captured image information of a sample dyed with a fluorescent dye reagent;
  acquiring information related to the fluorescent dye reagent;
  correcting luminance of the captured image information using a fluorescence fading coefficient that represents rapidness at which a fluorescence intensity of the fluorescent dye reagent drops, the fluorescence fading coefficient being included in the information related to the fluorescent dye reagent; and calculating information corresponding to fluorescent molecules in the captured image information, using the corrected luminance.

(13) An information processing system comprising:

an image acquiring unit that acquires captured image information of a sample dyed with a fluorescent dye reagent;

an information acquiring unit that acquires information related to the fluorescent dye reagent;

a correcting unit that corrects luminance of the captured image information using a fluorescence fading coefficient that represents rapidness at which a fluorescence intensity of the fluorescent dye reagent drops, the fluorescence fading coefficient being included in the information related to the fluorescent dye reagent;

a calculating unit that calculates information corresponding to fluorescent molecules in the captured image information, using the corrected luminance; and a display unit that displays image information generated based on the information corresponding to fluorescent molecules.

REFERENCE SIGNS LIST 10 fluorescent dye reagent
11 reagent identification information
20 sample
30 fluorescent dye sample
100 information processing apparatus
110 acquiring unit
111 information acquiring unit
112 image acquiring unit
120 storage unit
121 information storage unit
122 image information storage unit
130 processing unit
131 correcting unit
132 calculating unit
133 image generating unit
140 display unit
150 control unit
160 operation unit
200 database

The invention claimed is:

1. A method for generating an image, the method comprising:

determining a corrected luminance of pixels of an image of a sample dyed with a fluorescent dye reagent based on a fluorescence fading coefficient, the fluorescence fading coefficient representative of rapidness at which a fluorescence intensity of the fluorescent dye reagent decreases;

converting the corrected luminance of pixels into at least one of a first number of fluorescent molecules or a second number of antibodies bonded to the fluorescent molecules; and outputting image information based on at least one of the first number of fluorescent molecules or the second number of antibodies.

2. The method of claim 1, further including obtaining the fluorescence fading coefficient corresponding to the fluorescent dye reagent.

3. The method of claim 1, wherein at least one of the fluorescence intensity or the corrected luminance is a continuous value, and the first number of fluorescent molecules or the second number of antibodies is a discrete value.

4. The method of claim 1, further including obtaining at least one of a quantum yield, an absorption cross section, a molar absorbance coefficient, or a fluorescent labeling ratio associated with the fluorescent dye reagent.

5. The method of claim 4, wherein the obtaining of the at least one of the quantum yield, the absorption cross section, the molar absorbance coefficient, or the fluorescent labeling ratio is based on reagent identification information that identifies the fluorescent dye reagent.

6. The method of claim 5, wherein the reagent identification information identifies a production lot of the fluorescent dye reagent.

7. The method of claim 1, further including displaying the image information on a display device.

8. The method of claim 1, wherein the fluorescence fading coefficient is based on a number of photons absorbed by a fluorescent substance in the fluorescent dye reagent or a probability at which fluorescence of the fluorescent substance fades per excitation power density.

9. The method of claim 1, wherein the sample is a first sample, and the method further including determining the fluorescence fading coefficient based on a second sample different from the first sample.

10. The method of claim 1, wherein the determining of the corrected luminance is based on a correction associated with fluorescence saturation.

11. The method of claim 1, further including obtaining a measurement of excitation power density associated with the image, the measurement of excitation power density based on at least one of a measured energy emitted from a light source or an area irradiated with an excitation ray.

12. The method of claim 1, wherein the fluorescence fading coefficient is based on an excited photon density and an absorption cross section.

13. The method of claim 1, wherein the corrected luminance is based on an exposure time associated with capturing of the image.

14. The method of claim 1, further including:

converting the corrected luminance of pixels into a third number of photons; and converting the third number of photons into the at least one of the first number of fluorescent molecules or the second number of antibodies.

15. The method of claim 1, further including:

determining a third number of photons at a first pixel of the pixels based on a fourth number of electrons at the first pixel and a quantum yield of an imaging device that captures the image; and determining the at least one of the first number of fluorescent molecules or the second number of antibodies bonded to the fluorescent molecules based on the third number of photons.

16. The method of claim 1, further including capturing the image with a charge-coupled device or a complementary metal oxide semiconductor.

17. The method of claim 1, further including:

determining a third number of fluorescent molecules at a first pixel of the pixels based on a fourth number of photons detected at the first pixel and a fifth number of emitted photons per fluorescent molecule, the first number of fluorescent molecules based on the third number of fluorescent molecules; and determining a sixth number of antibodies based on the third number of fluorescent molecules at the first pixel and a fluorescent labeling ratio, the second number of antibodies based on the sixth number of antibodies.

18. A non-transitory computer readable storage medium comprising instructions
that, when executed, cause a processor to at least:
determine a corrected luminance of pixels of an image of a sample dyed with a fluorescent dye reagent based on a fluorescence fading coefficient, the fluorescence fading coefficient representative of rapidness at which a fluorescence intensity of the fluorescent dye reagent decreases;
convert the corrected luminance of pixels into at least one of a first number of fluorescent molecules or a second number of antibodies bonded to the fluorescent molecules; and
generate image information based on at least one of the first number of fluorescent molecules or the second number of antibodies.

19. An apparatus comprising:
memory;
a computer-readable program; and
a processor to execute the computer-readable program to at least:
determine a corrected luminance of pixels of an image of a sample dyed with a fluorescent dye reagent based on a fluorescence fading coefficient, the fluorescence fading coefficient representative of rapidness at which a fluorescence intensity of the fluorescent dye reagent decreases;
convert the corrected luminance of pixels into at least one of a first number of fluorescent molecules or a second number of antibodies bonded to the fluorescent molecules; and
generate image information based on at least one of the first number of fluorescent molecules or the second number of antibodies.

20. A system comprising:
a storage disc or storage device;
a computer-readable program stored in the storage disc or storage device;
a processor to execute the computer-readable program to:
determine a corrected luminance of pixels of an image of a sample dyed with a fluorescent dye reagent based on a fluorescence fading coefficient, the fluorescence fading coefficient representative of rapidness at which a fluorescence intensity of the fluorescent dye reagent decreases;
convert the corrected luminance of pixels into at least one of a first number of fluorescent molecules or a second number of antibodies bonded to the fluorescent molecules; and
output image information based on at least one of the first number of fluorescent molecules or the second number of antibodies; and
a display to display the image information.

* * * * *